US011298591B2

(12) United States Patent
Evancha et al.

(10) Patent No.: US 11,298,591 B2
(45) Date of Patent: Apr. 12, 2022

(54) EXERCISE MACHINE CONTROLS

(71) Applicant: Peloton Interactive, Inc., New York, NY (US)

(72) Inventors: Betina Evancha, Brooklyn, NY (US); Joseph Intonato, Brooklyn, NY (US); Ashley Willhite, Brooklyn, NY (US); Jooyoung Lee, Jersey City, NJ (US)

(73) Assignee: PELOTON INTERACTIVE, INC., New York, NY (US)

( * ) Notice: Subject to any disclaimer, the term of this patent is extended or adjusted under 35 U.S.C. 154(b) by 0 days.

(21) Appl. No.: 16/217,548

(22) Filed: Dec. 12, 2018

(65) Prior Publication Data

US 2019/0111318 A1 Apr. 18, 2019

Related U.S. Application Data

(63) Continuation-in-part of application No. 15/863,057, filed on Jan. 5, 2018, which is a continuation-in-part (Continued)

(51) Int. Cl.
*A63B 24/00* (2006.01)
*A63B 22/02* (2006.01)
*A63B 71/06* (2006.01)

(52) U.S. Cl.
CPC .......... *A63B 24/0087* (2013.01); *A63B 22/02* (2013.01); *A63B 22/025* (2015.10);
(Continued)

(58) Field of Classification Search
CPC ............ A63B 22/0087; A63B 22/0076; A63B 71/0622; A63B 21/023; A63B 2230/75;
(Continued)

(56) References Cited

U.S. PATENT DOCUMENTS 3,976,192 A 8/1976 Muller
4,614,337 A 9/1986 Schonenberger
(Continued)

FOREIGN PATENT DOCUMENTS

CN 2877780 3/2007
CN 105409145 A 3/2016
(Continued)

OTHER PUBLICATIONS

The PCT Search Report and Written Opinion dated Dec. 13, 2017, for PCT Application No. PCT/US2017/48650, 14 pages.
(Continued)

*Primary Examiner* — Garrett K Atkinson
(74) *Attorney, Agent, or Firm* — Haynes and Boone, LLP

(57) ABSTRACT

A method includes receiving electronic content via a network, the electronic content comprising an exercise class, and receiving user data associated with a user participating in the exercise class using an exercise machine. The method also includes generating an executable control for a user interface based at least in part on the user data, and providing the executable control, via a display of the exercise machine, while the user is participating in the exercise class. In such a method, the executable control is operable to modify a parameter of the exercise machine while the user is participating in the exercise class.

20 Claims, 8 Drawing Sheets

Related U.S. Application Data of application No. 15/686,875, filed on Aug. 25, 2017, now Pat. No. 10,864,406.

(60) Provisional application No. 62/380,412, filed on Aug. 27, 2016.

(52) U.S. Cl.
CPC .. *A63B 71/0622* (2013.01); *A63B 2024/0068* (2013.01); *A63B 2024/0081* (2013.01); *A63B 2024/0093* (2013.01); *A63B 2071/063* (2013.01); *A63B 2071/068* (2013.01); *A63B 2071/0658* (2013.01); *A63B 2209/00* (2013.01); *A63B 2225/20* (2013.01)

(58) Field of Classification Search
CPC ...... A63B 2225/107; A63B 2024/0081; A63B 21/00065; A63B 21/0428; A63B 2220/30; A63B 2071/063; A63B 2071/0081; A63B 2225/20; A63B 21/153; A63B 21/225; A63B 2071/0655; A63B 2208/0204; A63B 2022/0079; A63B 2208/0233; A63B 2225/50; A63B 2225/09; A63B 2220/20; A63B 24/0087; A63B 22/02; A63B 22/025; A63B 2071/0658; A63B 2024/0093; A63B 2024/0068; A63B 2071/068; A63B 22/0605; A63B 22/0664; A63B 24/0062; A63B 24/0075; A63B 2230/01; A63B 2230/40; A63B 2071/0641; A63B 2209/00; A63B 2071/0683; A63B 2225/105; A63B 2220/18; A63B 2220/17; A63B 2071/0625; A63B 2220/836; A63B 2220/34; A63B 71/0686; A63B 2220/833; A63B 2220/50; A63B 71/0669; A63B 2230/06; A63B 2071/065; A63B 2071/0691; A63B 2230/30; A63B 2071/0694; A63B 2230/50; A63B 2220/808; A63B 2220/806; A63B 2220/40; A63B 2220/62; A63B 24/0084; A63B 2220/80; A63B 71/0616; A63B 2024/0078; A63B 71/0619; G06F 19/3481; G09B 19/0038; G06Q 10/0639

See application file for complete search history.

(56) References Cited

U.S. PATENT DOCUMENTS

| | | | |
|---|---|---|---|
| 4,771,148 A | 9/1988 | Bersonnet | |
| D303,414 S | 9/1989 | Armstrong et al. | |
| D330,399 S | 10/1992 | Furline | |
| 5,178,594 A | 1/1993 | Wu | |
| 5,336,145 A | 8/1994 | Keiser | |
| 5,441,468 A | 8/1995 | Deckers et al. | |
| 5,458,548 A | 10/1995 | Crossing et al. | |
| 5,547,439 A | 8/1996 | Rawls et al. | |
| 5,656,000 A | 8/1997 | Russell | |
| 5,947,868 A | 9/1999 | Dugan | |
| 5,984,838 A | 11/1999 | Wang et al. | |
| 5,989,161 A | 11/1999 | Wang et al. | |
| 6,042,514 A | 3/2000 | Abelbeck | |
| 6,050,924 A | 4/2000 | Shea | |
| 6,171,218 B1 | 1/2001 | Shea | |
| 6,231,482 B1 | 5/2001 | Thompson | |
| 6,409,633 B1 | 6/2002 | Abelbeck | |
| 6,601,016 B1 | 7/2003 | Brown et al. | |
| 6,626,803 B1* | 9/2003 | Oglesby | A63B 22/02 482/51 |
| 6,648,798 B2 | 11/2003 | Yoo | |
| 6,702,719 B1 | 3/2004 | Brown et al. | |
| 6,749,536 B1 | 6/2004 | Cuskaden et al. | |
| 6,764,430 B1 | 7/2004 | Fencel | |
| 6,830,541 B2 | 12/2004 | Wu | |
| 6,899,659 B2 | 5/2005 | Anderson et al. | |
| 6,902,513 B1* | 6/2005 | McClure | A63B 24/0006 482/4 |
| 6,997,853 B1 | 2/2006 | Cuskaden et al. | |
| 7,153,241 B2 | 12/2006 | Wang | |
| 7,252,624 B2 | 8/2007 | Wu et al. | |
| 7,455,620 B2 | 11/2008 | Frykman et al. | |
| 7,562,761 B2 | 7/2009 | Tasma et al. | |
| 7,594,878 B1 | 9/2009 | Joannou | |
| 7,618,352 B1 | 11/2009 | Wei | |
| D606,599 S | 12/2009 | Murray et al. | |
| 7,628,730 B1 | 12/2009 | Watterson et al. | |
| 8,012,067 B2 | 9/2011 | Joannou | |
| 8,348,813 B2 | 1/2013 | Huang | |
| 8,608,624 B2 | 12/2013 | Shabodyash et al. | |
| 8,801,578 B2* | 8/2014 | Corbalis | A63B 22/02 482/9 |
| 8,829,376 B2 | 9/2014 | Wei | |
| 8,986,169 B2 | 3/2015 | Bayerlein et al. | |
| 9,174,085 B2 | 11/2015 | Foley et al. | |
| 9,254,411 B1 | 2/2016 | Chang | |
| 9,295,878 B2* | 3/2016 | Corbalis | A63B 24/0075 |
| 9,452,314 B2 | 9/2016 | Hou | |
| 9,463,349 B1 | 10/2016 | Chang | |
| 9,579,544 B2 | 2/2017 | Watterson | |
| 9,616,278 B2 | 4/2017 | Olson | |
| 9,636,567 B2 | 5/2017 | Brammer et al. | |
| 9,649,528 B2 | 5/2017 | Hou | |
| 9,675,839 B2 | 6/2017 | Dalebout et al. | |
| 9,682,307 B2 | 6/2017 | Dalebout | |
| 9,694,234 B2 | 7/2017 | Dalebout et al. | |
| 9,694,242 B2 | 7/2017 | Ashby et al. | |
| 9,713,742 B2 | 7/2017 | Pasini et al. | |
| 9,767,785 B2 | 9/2017 | Ashby et al. | |
| 9,808,672 B2 | 11/2017 | Dalebout | |
| 9,814,929 B2 | 11/2017 | Moser | |
| 9,814,930 B2 | 11/2017 | Manzke et al. | |
| 2002/0091627 A9 | 7/2002 | Fang | |
| 2004/0166995 A1 | 8/2004 | Wu | |
| 2005/0054490 A1 | 3/2005 | Chou | |
| 2005/0239601 A1* | 10/2005 | Thomas | H04L 67/12 482/1 |
| 2007/0032345 A1* | 2/2007 | Padmanabhan | G16H 40/40 482/8 |
| 2007/0072743 A1 | 3/2007 | Severino et al. | |
| 2007/0105693 A1 | 5/2007 | Wang | |
| 2007/0219059 A1* | 9/2007 | Schwartz | A61B 7/003 482/8 |
| 2007/0281831 A1 | 12/2007 | Wang | |
| 2008/0242511 A1 | 10/2008 | Munoz et al. | |
| 2010/0160115 A1* | 6/2010 | Morris | A63B 22/0235 482/4 |
| 2011/0319229 A1* | 12/2011 | Corbalis | A63B 71/0622 482/9 |
| 2012/0088633 A1 | 4/2012 | Crafton | |
| 2013/0281241 A1 | 10/2013 | Watterson et al. | |
| 2014/0038781 A1* | 2/2014 | Foley | G06F 19/3481 482/9 |
| 2014/0082526 A1 | 3/2014 | Park et al. | |
| 2014/0315690 A1* | 10/2014 | Corbalis | A63B 22/02 482/9 |
| 2015/0182800 A1 | 7/2015 | Watterson | |
| 2015/0238817 A1* | 8/2015 | Watterson | G06F 19/3481 482/8 |
| 2016/0023045 A1 | 1/2016 | Dalebout | |
| 2016/0023049 A1 | 1/2016 | Dalebout | |
| 2016/0103970 A1 | 4/2016 | Liu et al. | |
| 2016/0129311 A1* | 5/2016 | Yang | G16H 20/30 482/7 |
| 2016/0166877 A1 | 6/2016 | Cei et al. | |
| 2016/0181028 A1 | 6/2016 | Ebrom et al. | |
| 2016/0199695 A1 | 7/2016 | Armstrong | |
| 2017/0128769 A1* | 5/2017 | Long | A63B 22/0207 |
| 2017/0326411 A1 | 11/2017 | Watterson | |

(56) References Cited

U.S. PATENT DOCUMENTS

| | | |
|---|---|---|
| 2017/0340917 A1 | 11/2017 | Chang |
| 2018/0056132 A1 | 3/2018 | Foley et al. |
| 2018/0126248 A1 | 5/2018 | Dion et al. |
| 2018/0126249 A1 | 5/2018 | Consiglio et al. |
| 2018/0140903 A1 | 5/2018 | Poure et al. |

FOREIGN PATENT DOCUMENTS

| | | |
|---|---|---|
| CN | 205595259 U | 9/2016 |
| CN | 206544889 U | 10/2017 |
| EP | 0919259 | 6/1999 |
| EP | 2964349 | 1/2016 |
| TW | I644706 | 12/2018 |
| WO | WO199741925 | 11/1997 |
| WO | WO2005087323 | 9/2005 |
| WO | WO 2017/209500 | 12/2017 |
| WO | WO 2019/143488 | 7/2019 |

OTHER PUBLICATIONS

"CompuTrainer", Racermate, 2017, retrieved Nov. 30, 2018 from <<http://www.racermateinc.com/computrainer/>>, 1 page.

"Netathlon", WebRacing, 2014, retrieved Nov. 30, 2018 from <<http://webracinginc.com/products_netathlon.htm>>, 3 pages.

The PCT Search Report and Written Opinion dated Apr. 14, 2020 for PCT Application No. PCT/US2019/065882, 16 pages.

\* cited by examiner

EXERCISE MACHINE CONTROLS

CROSS-REFERENCE TO RELATED APPLICATIONS

The present application is a continuation-in-part of U.S. application Ser. No. 15/863,057, filed on Jan. 5, 2018, which is a continuation-in-part of U.S. application Ser. No. 15/686,875, filed on Aug. 25, 2017, which is a nonprovisional of U.S. Provisional Application No. 62/380,412, filed on Aug. 27, 2016, the entire disclosures of which are incorporated herein by reference.

FIELD OF THE INVENTION

This application relates generally to the field of exercise equipment and methods associated therewith. In particular, this application relates to executable controls and control methods associated with exercise machines.

BACKGROUND

Exercise has become an increasingly important aspect of daily life, and most exercise regimens commonly involve the use of elliptical machines, stationary bicycles, rowing machines, treadmills, or other exercise machines. Such exercise machines are typically designed for use in a gym or other exercise facility, and may be configured such that a user can participate in various exercise classes, training programs, or other activities using such machines. In particular, such exercise machines generally provide the user with one or more buttons, switches, knobs, levers, or other mechanisms that enable the user to control various parameters of the exercise machine during use. For instance, a treadmill may include one or more controls dedicated to increasing and decreasing an incline of the treadmill deck, increasing and decreasing a speed of the treadmill belt, or modifying other parameters of the treadmill as the user walks, jogs, sprints, or performs various other activities on the treadmill. Similarly, a stationary bicycle may include one or more controls dedicated to increasing and decreasing a braking resistance of a flywheel of the bicycle, increasing and decreasing a pedal speed or cadence of the bicycle, or modifying other parameters of the stationary bicycle during use.

While such controls are commonplace on treadmills, stationary bicycles, elliptical machines, and other known exercise machines, such controls can be challenging to use in some situations. For example, due to the dynamic nature of the motion-based activities typically performed on such exercise machines (e.g., running, cycling, etc.), it can be difficult for a user to manipulate such controls during a workout. Moreover, even if a user is able to manipulate such controls while running, cycling, or performing other motion-based activities, such controls may not be optimized for enabling the user to select a particular setting or other parameter of the exercise machine, with accuracy, as such motion-based activities are being performed.

Example embodiments of the present disclosure are directed toward addressing one or more of the deficiencies of known exercise machines noted above.

SUMMARY OF THE INVENTION

In an example embodiment of the present disclosure, a method includes receiving, with a processor associated with an exercise machine, electronic content via a network, the electronic content comprising an exercise class, receiving, with the processor, user data associated with a user participating in the exercise class using the exercise machine, and generating, with the processor, an executable control for a user interface based at least in part on the user data. The method also includes providing the executable control, via a display of the exercise machine, while the user is participating in the exercise class. In such examples, the executable control is operable to modify a parameter of the exercise machine while the user is participating in the exercise class.

In another example embodiment, an exercise machine includes a processor operably connected to a network, a display operably connected to the processor and configured to display electronic content received, by the processor, via the network, and a deck configured to move relative to a surface supporting the exercise machine. The exercise machine also includes a belt rotatable about the deck, a first motor operably connected to the processor and configured to drive the belt, and a second motor operably connected to the processor and configured to change a position of the deck relative to the support surface. In such an embodiment, the processor is configured to cause display of the electronic content via the display, the electronic content comprising an exercise class, receive user data associated with a user participating in the exercise class using the exercise machine, and generate an executable control based at least in part on the user data. The processor is also configured to provide the executable control, via the display, while causing the display of the electronic content. In such examples, the executable control is operable to modify a parameter of the exercise machine.

In yet another example embodiment, a method includes capturing audio content and video content corresponding to an exercise class being performed by an instructor, the exercise class being performed at least partially on a first exercise machine. Such a method may also include generating a video file comprising the audio content and the video content, generating an executable control corresponding to the exercise class, the executable control being operable to modify a parameter of a second exercise machine, and associating the executable control with the video file such that playback of at least part of the video file by a processor of the second exercise machine, via a display of the second exercise machine, results in display of the executable control. Such a method may also include providing the control, with the video file, to the processor of second exercise machine via a network.

BRIEF DESCRIPTION OF THE DRAWINGS

The detailed description is described with reference to the accompanying figures. In the figures, the left-most digit of a reference number identifies the figure in which the reference number first appears. The same reference numbers in different figures indicate similar or identical items.

DETAILED DESCRIPTION

Figure 1:
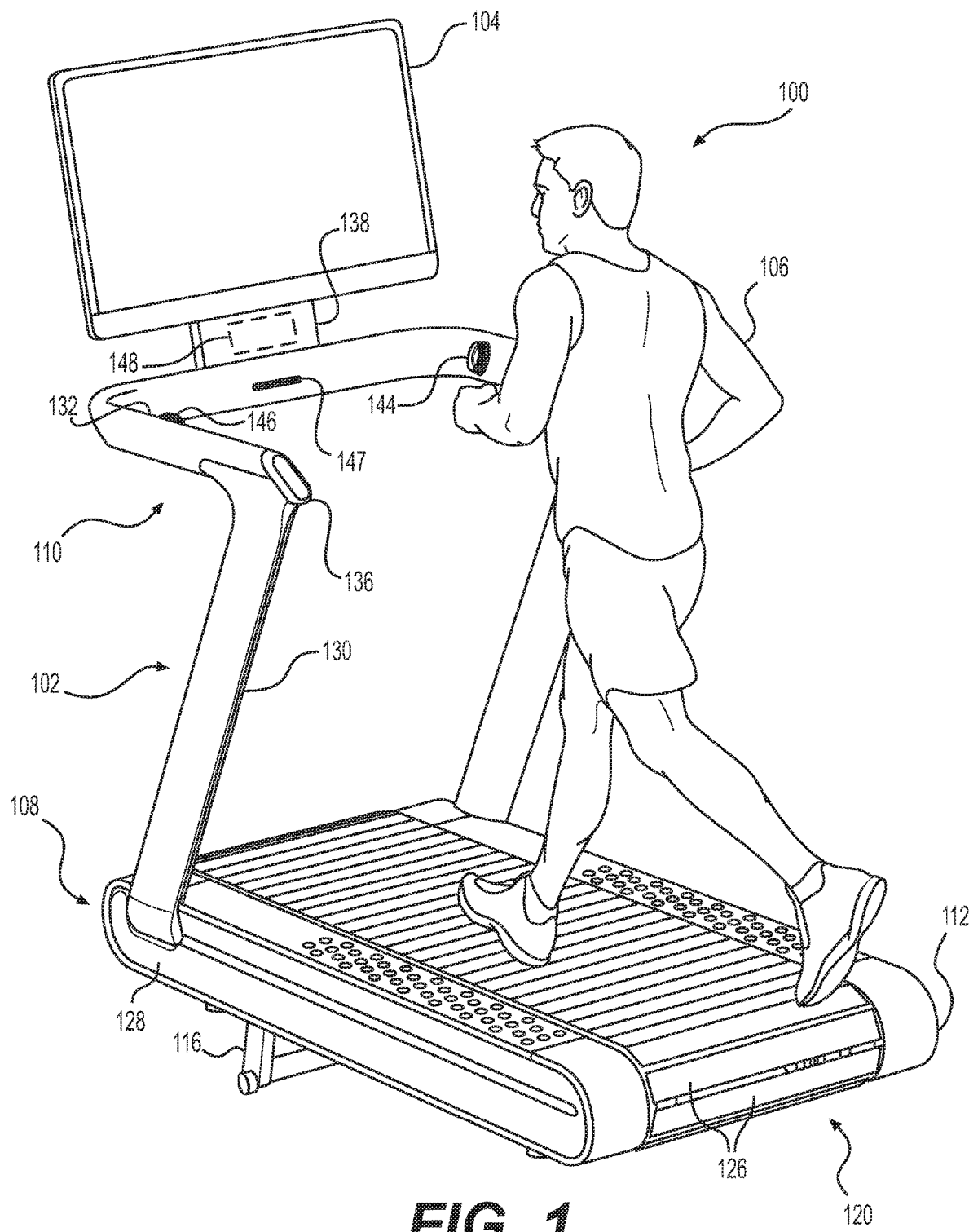
FIG. 1 is a perspective view of an example exercise machine as disclosed herein with a user shown.

The following description is presented to enable any person skilled in the art to make and use aspects of the example embodiments described herein. For purposes of explanation, specific nomenclature is set forth to provide a thorough understanding of the present invention. Descriptions of specific embodiments or applications are provided only as examples. Various modifications to the embodiments will be readily apparent to those skilled in the art, and general principles defined herein may be applied to other embodiments and applications without departing from the spirit and scope of the present disclosure. Thus, the present disclosure is not intended to be limited to the embodiments shown, but is to be accorded the widest possible scope consistent with the principles and features disclosed herein.

Example embodiments of the present disclosure include exercise machines, networked exercise systems, and corresponding methods whereby one or more exercise devices, such as treadmills, rowing machines, stationary bicycles, elliptical trainers, or any other suitable equipment may be equipped with an associated local system that allows a user to fully participate in live or recorded exercise classes from any location that can access a suitable communications network. The example exercise machines of the present disclosure include one or more displays configured to provide various controls operable to change parameters of the exercise machines. In particular, the displays of the present disclosure may be configured to provide user interfaces that include one or more executable controls operable to modify respective parameters of the exercise machine while the user of the machine is participating in an exercise class and/or otherwise using the exercise machine.

Such executable controls may be generated by a processor of the exercise machine and/or by one or more servers of a networked exercise system located remote from the exercise machine. In particular, such executable controls may be generated based on user data indicating one or more preferences of the user, one or more previous exercise machine settings selected by the user during one or more previous workouts, one or more exercise machine settings previously specified by the user as a preference and/or as part of a user profile unique to the user, and/or based on other user-specific information. Additionally or alternatively, such executable controls may be generated based on one or more commands uttered by an instructor of an exercise class. In some examples, such executable controls may include a setting corresponding to a relatively specific instruction or command given by the instructor. In other examples, on the other hand, such executable controls may include a setting corresponding to a relatively vague or abstract command given by the instructor during the exercise class. In still further examples, one or more executable controls of the present disclosure may be operable to modify a parameter of the exercise machine in order to assist the user in achieving one or more targets or exercise goals stored in a memory associated with the exercise machine.

Thus, the exercise machines, executable controls, and corresponding methods described herein, may enable a user to easily and accurately modify one or more parameters of an exercise machine while participating in an exercise class, and according to a control setting that is uniquely personal to the user. Various aspects of such exercise machines and executable controls will now be described in more detail.

Figure 2:
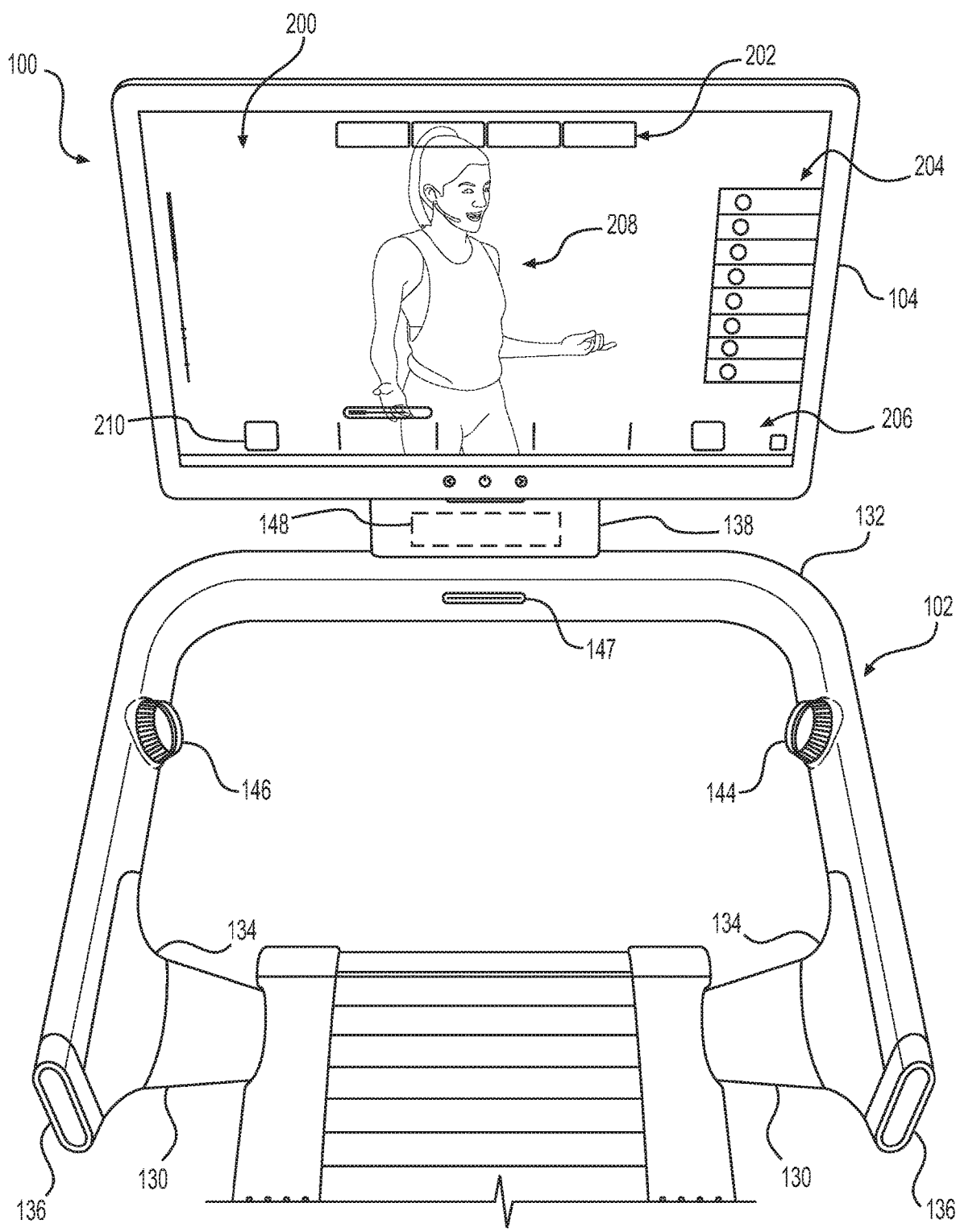
FIG. 2 illustrates another view of the example exercise machine shown in FIG. 1 including first and second rotary controls, and a display.

Referring generally to FIGS. 1 and 2, in various example embodiments of the present disclosure, a local system 100 may include an exercise machine 102, such as a treadmill, with integrated or connected digital hardware including one or more displays 104 for use in connection with an instructor-led exercise class and/or for displaying other digital content. While the exercise machine 102 may be described and/or otherwise referred to herein as a "treadmill 102," as noted above, example exercise machines 102 of the present disclosure may be any suitable type of exercise machine, including a rowing machine, stationary bicycle, elliptical trainer, stair climber, etc. Accordingly, any of the examples described herein may be applicable to, incorporated in, performed by, and/or otherwise associated with a treadmill, rowing machine, stationary bicycle, elliptical trainer, stair climber, etc. For ease of description, however, an exercise machine 102 comprising a treadmill will be referred to below unless otherwise specified.

In various example embodiments, the one or more displays 104 may be mounted directly to the exercise machine 102 or otherwise placed within view of a user 106. In various exemplary embodiments, the one or more displays 104 allow the user 106 to view content relating to a selected exercise class both while working out on the exercise machine 102 and while working out in one or more locations near or adjacent to the exercise machine 102. In some examples, the exercise machine 102 may also include a hinge, joint, pivot, bracket 138 or other suitable mechanism to allow for adjustment of the position or orientation of the display 104 relative to the user 106 whether the user 106 is working out on the exercise machine 102, or working out near or adjacent to the exercise machine 102.

In example embodiments in which the exercise machine 102 comprises a treadmill, the exercise machine 102 may generally include a lower assembly 108 and an upper assembly 110. The lower assembly 108 may generally include a deck 112 of the exercise machine 102 that provides support for the user 106 while the user 106 is working out on the exercise machine 102, as well as other components of both the lower assembly 108 and the upper assembly 110. For example, the deck 112 may support a first motor (not shown) of the exercise machine 102 configured to increase, decrease, and/or otherwise change an incline of the deck 112 relative to a support surface on which the exercise machine 102 is disposed. The deck 112 may also include one or more linkages 116 coupled to such a motor and configured to, for example, raise and lower the deck 112 by acting on the support surface when the motor is activated. The deck 112 may also include a second motor (not shown) configured to increase, decrease, and/or otherwise change a rotational speed of a belt 120 connected to the deck 112. The belt 120 may be rotatable relative to the deck 112 and, in particular, may be configured to revolve or otherwise move completely around (i.e., encircle) the deck 112 during use of the exercise machine 120. For example, in embodiments in which the exercise machine 102 comprises a treadmill, the belt 120 may support the user 106 and may repeatedly encircle the deck 112 as the user 106 runs, walks, and/or otherwise works out on the treadmill. Such an example belt 120 may include one or more continuous tracks (not shown) movably coupled to a gear, flywheel, pulley, and/or other component of the deck 112. In such examples, such a gear, flywheel, pulley, and/or other component of the deck 112 may be coupled to an output shaft or other component of the second motor described above. In such examples, rotation of the output shaft or other component of the second motor may drive commensurate rotation of the belt 120.

The belt 120 may also include a plurality of laterally aligned slats 126 connected to the one or more continuous tracks described above. For example, as shown in FIG. 1, each slat 126 may extend substantially parallel to at least one adjacent slat 126. Additionally, each slat 126 may be hingedly, pivotally, and/or otherwise movably coupled to the one or more continuous tracks of the deck 120 via one or more respective couplings. Such couplings may comprise, for example, a bracket, pin, screw, clip, bolt, and/or one or more other fastening components configured to secure a respective slat 126 to the continuous track described above, while allowing the slat 126 to pivot, rotate, and/or otherwise move relative to the track while the belt 120 revolves about the deck 112.

With continued reference to FIG. 1, the exercise machine 102 may also include one or more sidewalls 128 connected to the deck 112. For example, the exercise machine 102 may include a first sidewall 128 on a left-hand side of the deck 112, and a second sidewall 128 on the right-hand side of the deck 112. Such sidewalls 128 may be made from cloth, foam, plastic, rubber, polymers, and/or other like material, and in some examples, the sidewalls 128 may assist in damping and/or otherwise reducing noise generated by one or more of the motors and/or other components of the deck 112.

The exercise machine 102 may also include one or more posts 130 extending upwardly from the deck 112. For example, the exercise machine 102 may include a first post 130 on the left-hand side of the deck 112, and a second post 130 on the right-hand side of the deck 112. Such posts 130 may be made from a metal, alloy, plastic, polymer, and/or other like material, and similar such materials may be used to manufacture the deck 112, the slats 126, and/or other components of the exercise machine 102. In such examples, the posts 130 may be configured to support the display 104, and in some examples, the display 104 may be directly coupled to a crossbar 132 of the exercise machine 102, and the crossbar 132 may be connected to and/or otherwise supported by the posts 130. For example, the crossbar 132 may comprise one or more hand rests or handles useful in supporting the user 106 during exercise. In some examples, the crossbar 132 may be substantially C-shaped, substantially U-shaped, and/or any other configuration. In any of the examples described herein, the crossbar 132 may extend from a first one of the posts 130 to a second one of the posts 130. Further, in some examples, the posts 130 and the crossbar 132 may comprise a single integral component of the upper assembly 110. Alternatively, in other examples, the posts 130 and the crossbar 132 may comprise separate components of the upper assembly 110. In such examples, the upper assembly 110 may include one or more brackets 134, endcaps 136, and/or additional components configured to assist in coupling the one or more posts 130 to the crossbar 132.

As noted above, the exercise machine 102 may also include a hinge, joint, pivot, bracket 138 and/or other suitable mechanism to allow for adjustment of the position or orientation of the display 104 relative to the user 106 whether they are walking, jogging, running, and/or otherwise working out on the exercise machine 102, or working out near or adjacent to the exercise machine 102. For example, such brackets 138 may include at least one component rigidly connected to the crossbar 132. Such brackets 138 may also include one or more additional components rigidly coupled to the display 104. In such examples, the components of the bracket 138 connected to the display 104 may be moveable, with the display 104 relative to the components of the bracket 138 connected to the crossbar 132. Such components may include one or more dove-tail slider mechanism, channels, and/or other components enabling the display 104 to controllably slide and/or otherwise move relative to the crossbar 132. Such components may also enable the user 106 to fix the position of the display 104 relative to the crossbar 132 once the user 106 has positioned the display 104 as desired.

As shown in FIGS. 1 and 2, the exercise machine 102 may also include one or more controls 144, 146 configured to receive input from the user 106. The exercise machine 102 may further include one or more sensors 147 configured to sense, detect, and/or otherwise determine one or more performance parameters of the user 106 before, during, and/or after the user 106 participates in an exercise class using the exercise machine 102. In any of the examples described herein, the controls 144, 146 and the one or more sensors 147 may be operably and/or otherwise connected to one or more controllers, processors, and/or other digital hardware 148 of the exercise machine 102.

The digital hardware 148 (shown in phantom in FIGS. 1 and 2) associated with the exercise machine 102 may be connected to or integrated with the exercise machine 102, or it may be located remotely and wired or wirelessly connected to the exercise machine 102. The digital hardware 148 may include digital storage (e.g., a hard drive or other such memory), one or more processors (e.g., a microprocessor) or other like computers or controllers, communications hardware, software, and/or one or more media input/output devices such as displays, cameras, microphones, keyboards, touchscreens, headsets, and/or audio speakers. In various exemplary embodiments these components may be connected to and/or otherwise integrated with the exercise machine 102. All communications between and among such components of the digital hardware 148 may be multichannel, multi-directional, and wireless or wired, using any appropriate protocol or technology. In various exemplary embodiments, the digital hardware 148 of the exercise machine 102 may include associated mobile and web-based application programs that provide access to account, performance, and other relevant information to users from local or remote exercise machines, processors, controllers, personal computers, laptops, mobile devices, or any other digital device or digital hardware. In any of the examples described herein, the one or more controllers, processors, and/or other digital hardware 148 associated with the exercise machine 102 may be operable to perform one or more functions associated with control logic of the exercise machine 102. Such control logic may comprise one or more rules, programs, or other instructions stored in a memory of the digital hardware 148. For example, one or more processors included in the digital hardware 148 may be programmed to perform operations in accordance with rules, programs, or other instructions of the control logic, and such processors may also be programmed to perform one or more additional operations in accordance with and/or at least partly in response to input received via one or more of the controls 144, 146, via one or more of the sensors 147, and/or via various controls, user interfaces, or other components provided by the display 104. In any of the examples described herein, the display 104 may comprise a touch screen, a touch-sensitive (e.g., capacitance-sensitive) display, and/or any other device configured to display content and receive input (e.g., a touch input, tap input, swipe input, etc.) from the user 106.

In any of the examples described herein, one or more of the controls 144, 146 associated with the exercise machine 102 may comprise an infinity wheel-type control. Such a control may be useful in changing and/or otherwise controlling, for example, the incline of the deck 112, the speed of the belt 120, and/or other parameters of the exercise machine 102 associated with incremental increases or decreases. In an example embodiment, one or more of the controls 144, 146 associated with the exercise machine 102 may include a rotary dial connected to a corresponding rotary encoder. In such examples, the rotary encoder may include one or more detents or other components/structures that may be tuned for a desired incremental change in a corresponding parameter of the exercise machine 102. For example, the rotary encoder may be tuned such that each detent thereof may correlate to a 0.5% increase or decrease in an incline angle of the deck 112. Alternatively, the rotary encoder may be tuned such that each detent thereof may correlate to a 0.1 mph increase or decrease in a speed of the belt 120. In still further examples, percentages, speeds, and/or other increments greater than or less than those noted above may be chosen. Additionally, one or more such controls 144, 146 may include one or more additional buttons, wheels, touch pads, levers, knobs, or other components configured to receive additional inputs from the user 106, and such additional components may provide the user 106 with finer control over the corresponding parameters of the exercise machine 102. One or more such controls 144, 146 may also include a respective control housing configured to assist in mounting the control 144, 146 to the crossbar 132 or other components of the exercise machine 102.

With continued reference to FIGS. 1 and 2, in various example embodiments, the one or more sensors 147 of the exercise machine 102 may be configured to sense, detect, measure, and/or otherwise determine a range of user data, parameters of the exercise machine 102, and/or other information, from both the exercise machine 102 and the user 106, instantaneously and/or over time. For example, the exercise machine 102 may include one or more sensors 147 that measure the incline of the deck 112, the speed of the belt 120, a load applied to the deck 112, the belt 120, one or more of the motors described above, and/or other components of the exercise machine 102, an amount of energy expended by the user 106, a power output of the exercise machine 102, user weight, steps, distance, total work, repetitions, an amount of resistance applied to the belt 120 by one or more of the motors described above and/or other components of the exercise machine 102, a pedal cadence, a brake force or resistance, as well as any other information associated with, for example, a treadmill, a stationary bicycle, or other exercise machine 102. The exercise machine 102 may also include sensors 147 to measure user heart-rate, respiration, hydration, calorie burn, or any other physical performance metrics, or to receive such information from sensors provided by (e.g., worn by) the user 106. Where appropriate, such information can be calculated as current/instantaneous values, maximum, minimum, average, or total over time, or using any other statistical analysis. Trends can also be determined, stored, and displayed to the user, the instructor, and/or other users. Such sensors 147 may communicate with memory and/or processors of the digital hardware 148 associated with the exercise machine 102, nearby, or at a remote location, using wired or wireless connections. Such sensors 147 and/or the processors of the digital hardware 148 may also communicate with one or more processors disposed remote from the exercise machine 102 using such wired or wireless connections.

In various exemplary embodiments, the exercise machine 102 may also include one or more indicators (not shown) to provide information to the user 106. Such indicators may include lights, projected displays, speakers for audio outputs, or other output devices capable of providing a signal to a user 106 to provide the user 106 with information such as timing for performing an exercise, time to start or stop exercise, or other informational indicators. For example, such indicators (e.g., lights or projected displays) could display information regarding the number of sets and repetitions performed by the user 106 at a location where it can be seen by the user 106 during the performance of the relevant exercise.

With reference to FIG. 2, and as noted above, the display 104 of the exercise machine 100 may comprise and/or may be driven by a user input device such as a touchscreen, mouse, voice control, or other suitable input device. In some examples, the display 104 or at least a portion thereof, may comprise a touchscreen configured to receive touch input from the user 106. The display 104 may be any size, but optimally are large enough and oriented to allow the display of a range of information including one or more video streams, a range of performance metrics corresponding to the user 106, a range of additional performance metrics associated with one or more additional users exercising on exercise machines remote from the exercise machine 102, and a range of different controls. In various exemplary embodiments, the display 104 may include some or all of its area that can reflect the image of the user 106 to provide user feedback regarding their form and performance of various activities.

In various exemplary embodiments the user 106 can use the display 104 or one or more user interfaces 200 displayed on the display 104 to selectively present a range of different information including live and/or archived video, performance data, and other user and system information. In any of the examples described herein, such user interfaces 200 can provide a wide range of control and informational windows that can be accessed and removed individually and/or as a group by a click, touch, voice command, or gesture. In various exemplary embodiments, such windows may provide information about the user's own performance and/or the performance of other participants in the same exercise class both past and present.

Example user interfaces 200 presented via the display 104 may be used to access member information, login and logout of the system 100, access live content such as live exercise classes and archived classes or other content. User information may be displayed in a variety of formats and may include historical and current performance and account information, social networking links and information, achievements, etc. The user interfaces described herein can also be used to access the system 100 to update a user profile (e.g., a user profile that is unique to the user 106) or member information, manage account settings such as information sharing, and/or to modify one or more settings of a control included in the user interface 200.

An example user interface 200 may also be presented on the one or more displays 104 to allow users to manage their experience, including selecting information to be displayed and arranging how such information is displayed on the display 104. Such a user interface 200 may present multiple types of information overlaid such that different types of information can be selected or deselected easily by the user

106. For example, performance metrics and/or other information may be displayed over video content using translucent or partially transparent elements so the video behind the information elements can be seen together with (i.e., simultaneously with) the performance metrics and/or other information itself. Further, example user interfaces 200 may present a variety of screens to the user 106 which the user 106 can move among quickly using the provided user input device, including by providing a touch input via the display 104.

In any of the examples described herein, the processor and/or other components of the digital hardware 148 may control the display 104 and/or otherwise cause the display 104 to display the various user interfaces 200 of the present disclosure. For example, the processor or other components of the digital hardware 148 may cause the display 104 to display a user interface 200 comprising a home screen that provides basic information about the system 100 and/or the exercise machine 102, as well as available options. Such a home screen may provide direct links to information such as scheduled classes, archived classes, a leaderboard, instructors, and/or profile and account information. The home screen may also provide direct links to content such as a link to join a particular class. The user 106 can navigate among the different portions of the home screen by selecting such links using the applicable input device such as by touching the display 104 at the indicated location, or by swiping to bring on a new screen. An example user interface 200 providing such a home screen may also provide other information relevant to the user 106 such as social network information, and navigation buttons that allow the user to move quickly among the different screens in the user interface 200.

In various example embodiments, one or more of the user interfaces 200 may include various components configured to provide information to the user 106 while the user 106 is participating in an exercise class. For example, as will be described in greater detail below, one or more example user interfaces 200 may include a timeline 202 (e.g., a segmented timeline) indicating portions of an exercise class being displayed on the display 104, and a position and/or location within the timeline corresponding to the current portion of the exercise class being displayed. An example user interface 200 may also include a scorecard 204, leaderboard, or other component providing rankings, output, exercise machine parameters, user data, and/or other information related to other users participating in (either in real time, or previously) the exercise class being displayed on the display 104. An example user interface 200 may further include various display bars 206 or other components providing performance metrics, performance information, and/or other user data associated with the user 106. Such information may include, for example, various settings or other parameters of the exercise machine 102 (e.g., a current incline of the deck 112, a current speed of the belt 120, a current pedal cadence of a stationary bicycle, a current braking force or resistance of the stationary bicycle, etc.), an output of the user 106, and/or other information corresponding to the user 106 participating in an exercise class. Additionally, in some examples the user interface 200 may include one or more executable controls 210 operable to modify an incline of the deck 112, a speed of the belt 120, a pedal cadence of a stationary bicycle, a braking force or resistance of the stationary bicycle, and/or other parameters of the exercise machine 102 while the user 106 is participating in an exercise class. As shown in at least FIG. 2, in such embodiments the timeline 202, scorecard 204, leaderboard, display bars 206, executable controls 210, and/or other components of the user interface 200 may be displayed on the display 104 together with (e.g., simultaneously with) content 208 comprising the exercise class that the use 106 is currently participating in.

In various exemplary embodiments, the user interfaces 200 described herein may be run through a local program or application using a local operating system such as an Android or iOS application, or via a browser-based system. Any of the performance metrics or other information described herein with respect to the various user interfaces 200 may also be accessed remotely via any suitable network such as the internet. For example, users 106 may be able to access a website from a tablet, mobile phone, computer, and/or any other digital device, and such users 106 may be able to review historical information, communicate with other participants, schedule classes, access instructor information, and/or view any of the information described herein with respect to the various user interfaces 200 through such a website.

Figure 3:
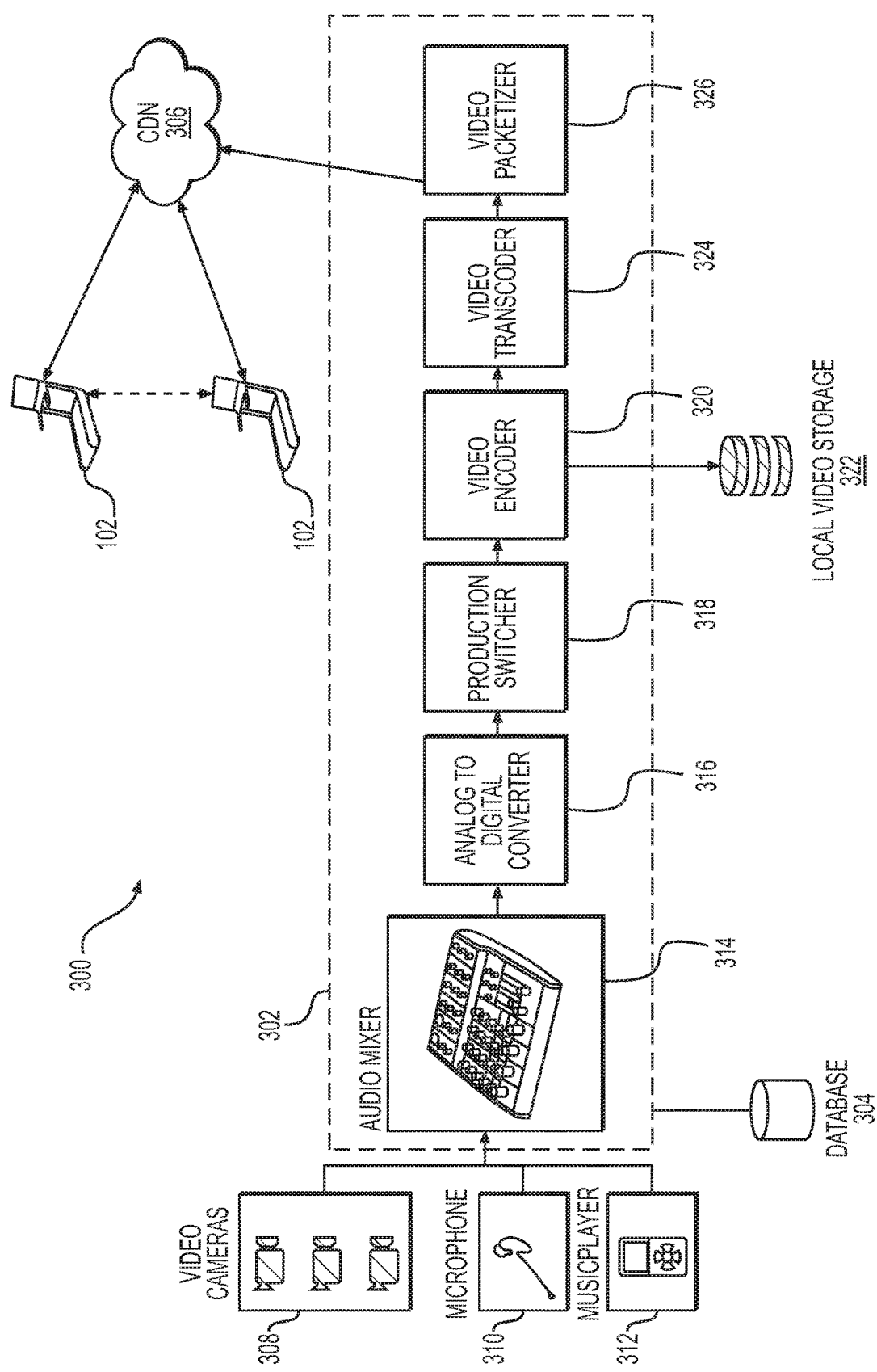
FIG. 3 is a schematic illustration showing exemplary components used for content creation and/or distribution.

FIG. 3 illustrates an example networked exercise system 300 of the present disclosure including one or more exercise machines 102 that are in communication via an example network. Such an example networked exercise system 300 may be used to, for example, capture and/or otherwise generate audio content, video content, and/or other content corresponding to an exercise class being performed by one or more instructors. The networked exercise system 300 may also be configured to generate a video file and/or any other electronic file, digital file, or the like comprising the captured audio content and video content. In some examples, the networked exercise system 300 may also be configured to generate one or more of the executable controls 210 described herein with respect to the user interface 200 (FIG. 2), and to associate such executable controls with the video file such that playback of at least part of the video file by a processor of an exercise machine 102 (e.g., via a display 104 of the exercise machine 102) may result in the display of the executable control 210. In any of the examples described herein, content captured and/or distributed by the networked exercise system 300 may comprise live and/or archived exercise classes, live and/or archived instructional content such as video content explaining how to properly perform an exercise, scenic or map-based content, videos, and/or animations that can be rendered in three-dimensions from any angle may be created and stored in various local or remote locations and shared across the networked exercise system 300.

In various example embodiments, the networked exercise system 300 may be managed through one or more networked backend servers 302 and may include various databases 304 for storage of user data, system information, performance information, archived content, etc. Example local systems 100 (FIG. 1) may be in communication with the networked backend servers 302 via any appropriate network 306 (e.g., a content distribution network 306), including without limitation, the internet. As an example of an alternative distribution approach, in various exemplary embodiments the backend servers 302 could be eliminated and data could be communicated throughout the system in a distributed or peer-to-peer manner rather than via a central server network. In such a networked exercise system 300, user data (e.g., performance data) may be broken up into small packets or "pieces" and distributed among user devices such that complete data sets are quickly distributed to all devices for display as required.

Content for distribution through the network 306 can be created in a variety of different ways. Content recording locations may include professional content recording studios, amateur and home-based locations, gyms, etc. In various exemplary embodiments, recording studios may include space for live instructor-led exercise classes with live studio participation, or may be dedicated studios with no live, in-studio participation. As shown in FIG. 3, recording equipment including one or more video cameras 308, microphones 310, mp3 players or other music players 312, and/or other components and can be used to capture the instructor and/or participants during the class. Multiple cameras 308 can provide different views, and 3D cameras 308 can be used to create 3D content. In various exemplary embodiments, content may also be generated locally by users 106. For example, exercise machines 102 may be equipped with recording equipment including microphones 310 and cameras 308. Users 106 may generate live or recorded classes that can be transmitted, stored in or by the networked exercise system 300, and distributed via the network 306.

With continued reference to FIG. 3, class content may be generated by providing outputs of the one or more video cameras 308, microphones 310, and/or music players 312 as inputs to an audio mixer 314. The audio mixer 314 may output content to an analog to digital converter 316, which may provide converted data to a production switcher 318. The production switcher 318 may send the production video to a video encoder 320, which may store the encoded video to a local storage device 322, and may also send it to a video transcoder 324.

In some examples, the video encoder 320 may receive input from one or more users of the backend servers 302 comprising a command to associate an executable control 210 with the video file being created by the networked exercise system 300. In such examples, the video encoder 320 may embed and/or otherwise associate such an executable control 210 with the video file, and at a desired location within the video file. Alternatively, the video encoder 320 and/or other components of the backend servers 302 may identify a verbal command from an instructor that is leading an exercise class. In such examples, the video encoder 320 and/or other components of the backend servers 302 may identify the verbal command included in audio content received from a microphone 310 and/or from a video camera 308. Such a command may correspond to a parameter of an exercise machine 102 (e.g., an incline of the deck 112, a speed of the belt 120, a pedal cadence of a stationary bicycle, a braking force or resistance of the stationary bicycle, etc.). In such examples, the video encoder 320 and/or other components of the backend servers 302 may identify a timestamp associated with the command (e.g., a timestamp in the video content and/or the audio content corresponding to the command). In such examples, the video encoder 320 and/or other components of the backend servers 302 may associate the executable control 210 with the video file by linking the executable control 210 to a part of the video file corresponding to the timestamp. Additionally in any of the examples described herein, the video encoder 320 and/or other components of the backend servers 302 may identify such a verbal command via natural language processing software or techniques.

Further, the video transcoder 324 may output transcoded data to a video packetizer 326, which may then send a packetized data stream out through the network 306 to remote users 106. In various exemplary embodiments, instructors and/or users 106 may be provided with access to a content creation platform that they can use to help them create content. Such a platform may provide tools for selecting and editing music, managing volume controls, pushing out chat or other communications to users 106.

As described above with respect to FIGS. 1 and 2, through the display 104 and/or other user interface on their exercise machine 102, users 106 may access lists, calendars, and schedules of live and recorded exercise classes available for delivery through the display 104. In various exemplary embodiments, once the user 106 selects a class, the local system 100 may access and/or display a primary data stream for the class. This primary data stream may include video, music, voice, text, or any other data, and may represent a live or previously recorded exercise class. The local system 100 may be equipped for hardware video accelerated encoding/decoding to manage high definition video quality at up to 1080 pixels based on existing technology. The local system 100 may automatically adjust bitrate/quality of the data stream for the class in order to bring participant the highest quality video according to user's bandwidth/hardware limitations.

In various exemplary embodiments, networked exercise systems 300 and methods of the present disclosure may include multi-directional communication and data transfer capabilities that allow video, audio, voice, and data sharing among all users 106 and/or instructors. This allows users 106 to access and display multi-directional video and audio streams from the instructor and/or other users regardless of location, and to establish direct communications with other users 106 to have private or conferenced video and/or audio communications during live or recorded classes. Such data streams can be established through the local system 100 for presentation via the one or more displays 104 via one or more of the user interfaces 200 described above. In various exemplary embodiments, users 106 can manage multiple data streams to select and control inputs and outputs. The local system 100 may allow the user 106 to control the volume of primary audio stream for the class as well as other audio channels for different users or even unrelated audio streams such as telephone calls or their own music selections. For example, this would allow a user 106 to turn down the instructor volume to facilitate a conversation with other users.

For live classes, in various exemplary embodiments the instructor may have the ability to communicate with the entire class simultaneously or to contact individual users, and solicit feedback from all users regardless of location in real-time. For example, instructors could ask users verbally, or text a pop-up message to users 106, seeking feedback on difficulty level, music choice, terrain, etc. Users 106 could then respond through components of the local system 100 by selecting an appropriate response, or providing verbal feedback. This allows instructors to use crowdsourcing to tailor a class to the needs of the participants, and to improve their classes by soliciting feedback or voting on particular class features or elements.

In various exemplary embodiments, instructors may also be able to set performance targets, and the system can measure and display to the user 106 and the instructor their performance relative to the target. For example, the instructor may set target metrics e.g. target power and speed, then display this next to users' readings with a color coding to indicate whether or not the user is meeting this target. The system may allow the instructor to remotely adjust exercise machine settings for individual users 106. In various exemplary embodiments, the exercise machine 102 may also automatically adjust based on information from the user 106, the instructor, or based on performance. For example, the exercise machine 102 may adjust the difficulty to maintain a particular performance parameter such as heart rate within a particular range or to meet a particular performance target. Any of the executable controls described herein may be generated and/or configured to modify a parameter of the exercise machine 102 in order to assist the user 106 in meeting and/or exceeding such performance goals or targets.

With continued reference to FIG. 3, in various exemplary embodiments, the networked exercise system 300 described herein may allow users 106 to create accounts (e.g., user profiles) and save and manage their user data (e.g., performance data). As discussed above, the system may allow users 106 to browse schedules for upcoming live classes, signup for future live streaming classes, and setup reminders. Users 106 may also be able to invite others to participate in a live class, and setup text, email, voice, or other notifications and calendar entries. Users 106 may be able to access system, account, performance, and all other data via web-based or application based interfaces for desktop and/or mobile devices, in addition to the user interface for the local system 100 associated with their exercise machine 102.

In various exemplary embodiments, the networked exercise system 300 can provide for simultaneous participation by multiple users in a recorded class, synchronized by the system and allowing access to all of the same communication and data sharing features that are available for a live class. With such a feature, the participants simultaneously participating in the same archived class can compete against each other, as well as against past performances or "ghost" participants for the same class. In some of the examples described herein, one or more executable controls may be generated and/or configured to modify a parameter of the exercise machine 102 in order to assist the user 106 in keeping pace with such past performances, "ghost" participants, and/or other performance goals or targets.

In some examples, the networked computer system 300 may be configured to feed synchronized live and/or archived video content and live and/or archived sensor data to users over the network 306. In various exemplary embodiments, and as illustrated in FIG. 3, the networked exercise system 300 may be configured with a plurality of user exercise machines 102 in communication with the video content distribution network 306. The user exercise machines 102 may also be in communication with various other networks and servers. Additionally, in any of the examples described herein, a control station (not shown) may provide signals via the network 306 to control the collection, storage, and management of data (e.g., user data, video content, audio content, parameters of the various exercise machines 102, etc.) across the networked exercise system 300.

Figure 4:
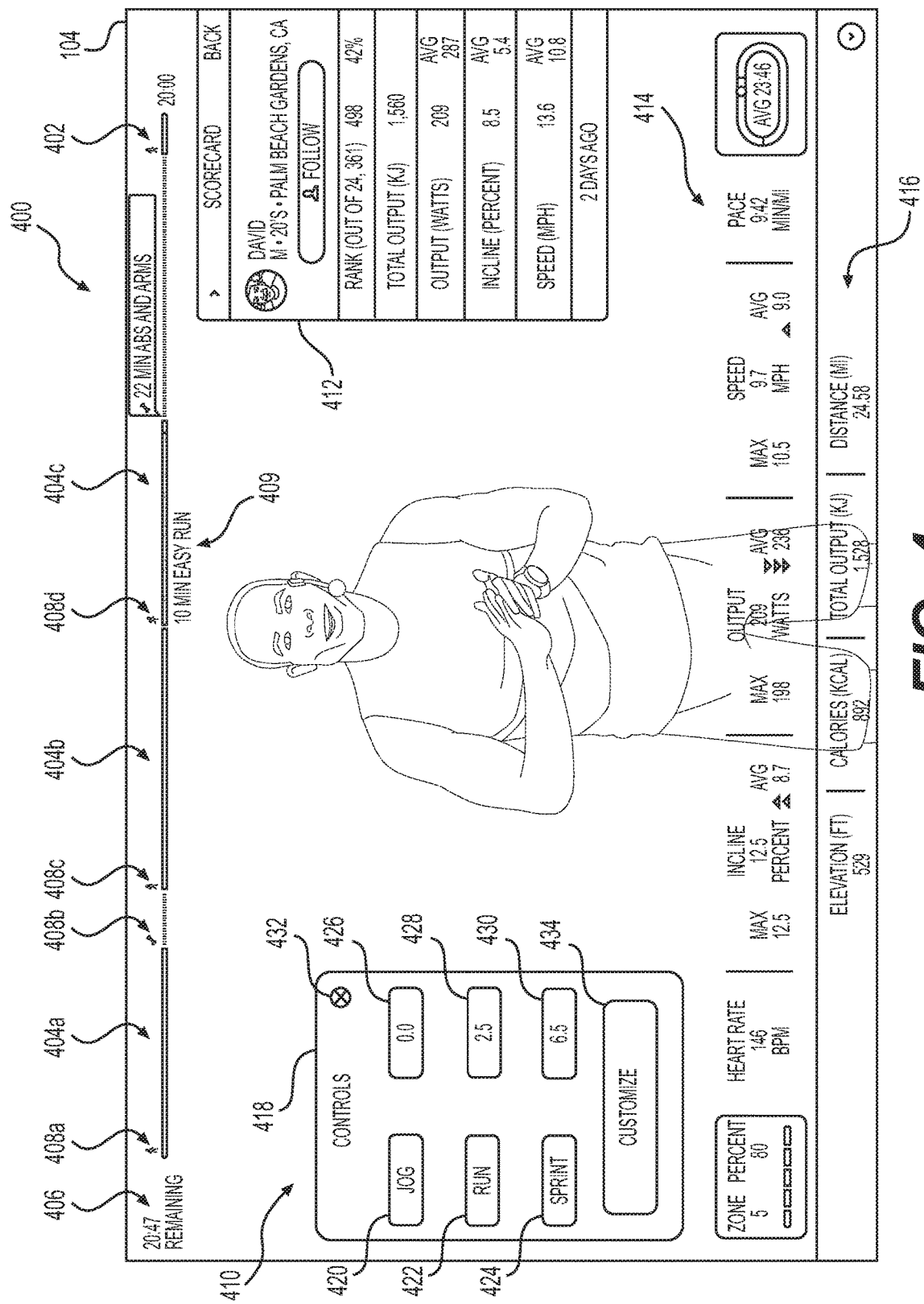
FIG. 4 illustrates an example user interface of the present disclosure showing an exercise class and a scorecard.

FIG. 4 illustrates an example user interface 400 of the present disclosure, and the user interface 400 may be similar to and/or the same as the user interface 200 described above with respect to FIG. 2. In such examples, the user interface 400 may be provided to the user 106 during a selected exercise class. When an exercise class is being displayed and/or otherwise provided via the one or more displays 104 through the user interface 400, in various exemplary embodiments the primary video feed may be shown as the background video full-screen or in a sub-window on the display 104. Information elements may be provided on different parts of the display screen to indicate any performance metrics, including total time, elapsed time, time left, distance, speed (e.g., speed of the belt 120), mile pace of the user 106, incline (e.g., incline of the deck 112), elevation, resistance, braking force, power, total work, energy expended (e.g., output), cadence (e.g., pedal cadence), heart rate, respiration, hydration, calorie burn, and/or any custom performance scores that may be developed. The displayed information may also include the trend or relationship between different performance metrics. For example, the display 104 can indicate a particular metric in a color that indicates current performance compared to average performance for an exercise class or over time, such as red to indicate that current performance of the user 106 is below average or green to indicate above average performance. Trends or relative performance can also be shown using color and graphics, such as a red down arrow to show that current performance is below average.

In various exemplary embodiments, the display 104 may also display information that supports or supplements the information provided by the instructor. Examples include one or more segmented timelines 402 that are illustrated together with at least part of the selected exercise class in the user interface 400. As shown in at least FIGS. 4 and 5, an example segmented timeline 402 may include one or more segments 404a, 404b, 404c . . . 404n (collectively, "segments 404") corresponding to respective portions, parts, or other exercise segments of the selected exercise class. The size, length, width, height, relative position, color, opacity, and/or other configurations of such segments 404 may be representative of, for example, the length of the corresponding portions or parts of the selected exercise class. The segmented timeline 402 may also provide an indication 406 of elapsed time and/or remaining time for the present workout segment and/or for the exercise class generally. The segmented timeline 402 may also include one or more visual indicia 408a, 408b, 408c . . . 408n (collectively, "indicia 408") indicating an activity requirement (e.g., run, jog, sprint, lift weights, etc.), an equipment requirement (e.g., dumbbells), and/or other requirement associated with a respective exercise segment of the selected exercise class. For example, the indicia 408a may indicate that the segment 404a comprises a walking segment, indicia 408d may indicate that the segment 404c comprises a running segment, and the indicia 408b may indicate that weights are required for at least part of the segment 404a. In any of the examples described herein, such segmented timelines 402 may also include one or more lists or windows identifying and/or describing upcoming workout segments or features, instructional information such as graphics or videos demonstrating how to properly perform exercises, or other information relevant to the exercise class in progress. Such segmented timelines 402 may also provide and/or otherwise include information 409 indicating the current segment of the exercise class and/or the current activity that the instructor is requesting the user 106 perform.

As shown in at least FIG. 4, the user interface 400 may include a primary window 410 configured to show the live or archived exercise class or other content that the user 106 selected. In various exemplary embodiments, the user interface 400 may further include one or more performance metric windows 412 (e.g., the "scorecard" illustrated in FIG. 4) overlaid on and/or otherwise displayed together with the primary window 410. Such performance metric windows 412 may show a ranking, total output, current output, incline, belt speed, mile pace, and/or other specific performance metrics for the user's current class, past classes, or other performance information. Such performance metric windows 412 may be presented anywhere on the display 104, and may be user selectable such that they can be displayed or removed by a screen touch or gesture.

The user interface 400 may also allow the user 106 to toggle between display of maximum, average, and total results for different performance metrics. Additionally, the user interface 400 may allow the user 106 to hide or display information elements, including performance metrics, video streams, user information, etc. all at once or individually. Performance metrics and/or other performance information can also be displayed in various display bars 414, 416 that can be hidden or displayed as a group or individually. The user interface 400 may provide for complete controls for audio volume, inputs, and outputs as well as display output characteristics.

In any of the examples described herein, the user interface 400 may also include one or more additional windows 418 overlaid on and/or otherwise displayed together with the primary window 410, and such additional windows 418 may include one or more executable controls operable to modify a parameter of the exercise machine 102 while the user 106 is participating in an exercise class. For example, as shown in FIG. 4, such an additional window 418 may include a plurality of executable controls configured to modify a speed of the belt 120, an incline of the deck 112, a resistance associated with the belt 120, a pedal cadence of a stationary bicycle, a braking force or resistance of the stationary bicycle, and/or other parameters of the exercise machine 102. For example, as illustrated in FIG. 4, in embodiments in which the exercise machine 102 comprises a treadmill, the window 418 may include a "jog" executable control 420, a "run" executable control 422, a "sprint" executable control 424, and/or other executable controls configured to modify a speed of the belt 120. In particular, such executable controls may be configured to receive one or more inputs from the user 106 while the user 106 is participating in an exercise class using the exercise machine 102. The "jog" executable control 420, "run" executable control 422, and "sprint" executable control 424 may be operable to modify the speed of the belt 120 based at least in part on such an input.

In such examples, the "jog" executable control 420 may be associated with a first speed of the belt 120 such that, upon receipt of a touch input via the executable control 420, the processor, and/or other digital hardware 148 of the exercise machine 102 may control the motor of the deck 112 driving the belt 120 to cause the belt 120 to rotate about the deck 112, at a speed corresponding to a jogging pace of the user 106. In some examples, the speed associated with the "jog" executable control 420 may be a default jogging pace stored in a memory of the digital hardware 148 and/or otherwise associated with the executable control 420. Alternatively, in other examples the speed associated with the "jog" executable control 420 may be customized, programmed, entered, and/or otherwise selected by the user 106, when establishing a user profile unique to the user 106, before the user 106 begins participating in the current exercise class, while the user 106 is participating in the exercise class, and/or at any other time. Accordingly, in such examples the user 106 may select a speed at which the user 106 desires the belt 120 to rotate when the user selects and/or otherwise, provides a touch input via the "jog" executable control 420. In such examples, the speed of the belt 120, and/or other parameter of the exercise machine 102 associated with the "jog" executable control 420 may be stored as part of the user profile of the user 106 in the memory associated with the digital hardware 148 and/or in, for example, the database 304 and/or other memory associated with the one or more servers 302 of the system 300 (FIG. 3).

In still further examples, the speed associated with the "jog" executable control 420 may be a speed that is identified, calculated, selected, and/or otherwise determined by, for example, the processor of the exercise machine 102, and/or a processor or other component of the one or more servers 306. In such further examples, the speed associated with the "jog" executable control 420 may be determined based on, for example, aggregate user data associated with past user selections, past user performances, or other previous workouts of the user 106. In such examples, for instance, the processor and/or other digital hardware 148 of the exercise machine 102 may sense, collect, and/or otherwise determine user data including belt speeds that the user 106 commonly selects during participation in exercise classes using the exercise machine 102. In such examples, the processor, and/or other digital hardware 148 of the exercise machine 102 may store such user data in a memory associated with the digital hardware 148. The processor may also select, identify, and/or otherwise determine a belt speed frequently selected by the user 106 based at least in part on such user data, and may associate the selected speed with the "jog" executable control 420. For instance, such a selected speed may be associated with a warm-up period/segment of previous exercise classes participated in by the user 106, and such a speed may comprise a speed most frequently selected by the user 106 during such previous warm-up periods/segments. As will be described in greater detail below, in further examples, one or more additional methods may be used by the processor of the digital hardware 148 in determining which speed to associate with the "jog" executable control 420.

It is understood that the "run" executable control 422, the "sprint" executable control 424, and/or other controls included in the window 418 may be configured in a similar fashion. For example, the "run" executable control 422 may be associated with a second speed of the belt 120 greater than the first speed described above with respect to the "jog" executable control 420. In such examples, upon receipt of a touch input via the executable control 422, the processor, and/or other digital hardware 148 of the exercise machine 102 may control the motor of the deck 112 driving the belt 120 to cause the belt 120 to rotate about the deck 112, at a speed corresponding to a running pace of the user 106. In some examples, the speed associated with the "run" executable control 420 may be a default running pace stored in a memory of the digital hardware 148 and/or otherwise associated with the executable control 422. Alternatively, in other examples the speed associated with the "run" executable control 420 may be entered, and/or otherwise selected by the user 106, when establishing a user profile unique to the user 106, before the user 106 begins participating in the current exercise class, while the user 106 is participating in the exercise class, and/or at any other time. Accordingly, in such examples the user 106 may select a speed at which the user 106 desires the belt 120 to rotate when the user selects and/or otherwise, provides a touch input via the "run" executable control 420. In such examples, the speed of the belt 120, and/or other parameter of the exercise machine 102 associated with the "run" executable control 420 may be stored as part of the user profile of the user 106 in the memory associated with the digital hardware 148 and/or in, for example, the database 304, and/or other memory associated with the one or more servers 302 of the system 300 (FIG. 3).

In still further examples, the speed associated with the "run" executable control 422 may be a speed that is identified, calculated, selected, and/or otherwise determined by, for example, the processor of the exercise machine 102, and/or a processor or other component of the one or more servers 306. In such further examples, the speed associated with the "run" executable control 422 may be determined based on, for example, aggregate user data associated with past performances, selections, or other workouts of the user 106. In such examples, for instance, the processor and/or other digital hardware 148 of the exercise machine 102 may sense, collect, and/or otherwise determine user data including belt speeds that the user 106 commonly selects during participation in exercise classes using the exercise machine 102. In such examples, the processor, and/or other digital hardware 148 of the exercise machine 102 may select, identify, and/or otherwise determine a frequently selected belt speed of the user 106 based at least in part on such user data, and may associate the selected speed with the "run" executable control 420. For instance, such a selected speed may be associated with a relatively long and/or sustained period/segment of previous exercise classes participated in by the user 106, and such a speed may comprise a speed most frequently selected by the user 106 during such previous relatively long and/or sustained periods/segments. As will be described in greater detail below, in further examples, one or more additional methods may be used by the processor of the digital hardware 148 in determining which speed to associate with the "run" executable control 420.

It is understood that similar methods and/or processes may also be used by the processor of the digital hardware 148 in determining which speed to associate with the "sprint" executable control 424. For instance, such a selected speed may be associated with a relatively short period/segment of previous exercise classes participated in by the user 106, and such a speed may comprise a top speed most frequently selected by the user 106 during such previous relatively short periods/segments.

As illustrated in FIG. 4 the window 418 may also include a plurality of additional executable controls 426, 428, 430 and/or other executable controls configured to modify an incline of the deck 112 and/or other parameters of the exercise machine 102. In particular, such executable controls 426, 428, 430 may be configured to receive one or more inputs from the user 106 while the user 106 is participating in an exercise class using the exercise machine 102, and such executable controls 426, 428, 430 may be operable to modify the incline of the deck 112 based at least in part on such an input. One or more of the executable controls 426, 428, 430 may be configured through a process similar to that described above with respect to the executable controls 420, 422, 424.

For example, the executable control 426 may be associated with a first incline of the deck 112, the executable control 428 may be associated with a second incline of the deck 428 greater than the first incline, and the executable control 430 may be associated with a third incline of the deck greater than both the first and second inclines. In such examples, upon receipt of a touch input via the executable control 426, the processor and/or other digital hardware 148 of the exercise machine 102 may control the motor of the deck 112 controlling the incline of the deck 112 to increase or decrease the incline of the deck 112 so that the incline of the deck 112 matches the incline associated with the executable control 426. The processor and/or other digital hardware 148 of the exercise machine 102 may also control the motor of the deck 112 controlling the incline of the deck 112 to increase or decrease the incline of the deck in a similar fashion in response to receipt of a touch input via the executable controls 428, 430.

In some examples, the respective inclines of the deck 112 associated with the executable controls 426, 428, 430 may comprise respective default inclines stored in a memory of the digital hardware 148 and/or otherwise associated with the executable controls 426, 428, 430. Alternatively, in other examples the respective inclines of the deck 112 associated with the executable controls 426, 428, 430 may be entered, customized, and/or otherwise selected by the user 106, when establishing a user profile unique to the user 106, before the user 106 begins participating in the current exercise class, while the user 106 is participating in the exercise class, and/or at any other time. Accordingly, in such examples the user 106 may select respective inclines at which the user 106 desires the deck 112 to be positioned, relative to a support surface on which the exercise machine 102 is disposed, when the user 106 selects and/or otherwise provides a touch input via the various executable controls 426, 428, 430. In such examples, the respective inclines of the deck 112 associated with the executable controls 426, 428, 430 may be stored as part of the user profile of the user 106 in the memory associated with the digital hardware 148 and/or in, for example, the database 304, and/or other memory associated with the one or more servers 302 of the system 300 (FIG. 3).

In still further examples, the respective inclines of the deck 112 associated with the executable controls 426, 428, 430 may comprise inclines that are identified, calculated, selected, and/or otherwise determined by, for example, the processor of the exercise machine 102, and/or a processor or other component of the one or more servers 306. In such further examples, the respective inclines of the deck 112 associated with the executable controls 426, 428, 430 may be determined based on, for example, aggregate user data associated with past performances or other workouts of the user 106. In such examples, for instance, the processor and/or other digital hardware 148 of the exercise machine 102 may sense, collect, and/or otherwise determine user data including deck incline settings that the user 106 commonly selects during participation in exercise classes using the exercise machine 102. In such examples, the processor, and/or other digital hardware 148 of the exercise machine 102 may store such user data in a memory associated with the digital hardware 148. The processor may also select, identify, and/or otherwise determine one or more deck inclines frequently selected by the user 106 based at least in part on such user data, and may associate one or more such deck inclines with the respective the executable controls 426, 428, 430. For instance, during a warm-up period/segment of multiple previous exercise classes participated in by the user 106, the user may choose to jog at a relatively flat deck incline. In such examples, a deck incline most frequently selected by the user 106 during such previous warm-up periods/segments may be approximately 0.0 (e.g., a substantially horizontal deck position relative to a support surface on which the exercise machine 102 is located). In such examples, the processor of the digital hardware 148 may select, identify, and/or otherwise determine such a deck incline frequently selected by the user 106 based at least in part on user data collected over multiple exercise classes participated in by the user 106 via the exercise machine 102. The processor of the digital hardware 148 may also associate such a deck incline with a respective one of the executable controls (e.g., with the executable control 426 shown in FIG. 4). The processor of the digital hardware 148 may associated respective deck inclines with the executable controls 428 and 430 in a similar manner. As will be described in greater detail below, in further examples, one or more additional methods may also be used by the processor of the digital hardware 148 in determining which deck incline to associate with the various executable controls 426, 428, 430 described herein. Additionally, as noted above, any of the processes described herein with respect to configuring, generating, providing, causing the display of, and/or modifying one or more of the executable controls 420, 422, 424, 426, 428, 430 may be performed locally at the exercise machine 102 by the processor of the digital hardware 148, remote from the exercise machine 102 by one or more processors of the server 302, and/or by the processor of the digital hardware 148 operating in communication and/or in conjunction with one or more processors of the server 302.

With continued reference to FIG. 4, in some examples the window 418 may include an executable control 432 operable to close the window 418 such that the window 418 (and the executable controls provided therein) is no longer displayed on the display 402. Additionally, in any of the examples described herein the window 418 and/or other portions of the user interface 400 may include an executable control 434 operable to enable the user 106 to customize one or more of the executable controls 420, 422, 424, 426, 428, 430 provided by the window 418. For example, the executable control 434 may be configured to receive a touch input from the user 106 indicative of a request to modify at least one setting of one or more of the executable controls 420, 422, 424, 426, 428, 430 provided by the window 418. Based at least in part on such an input, the processor of the digital hardware 148 may provide one or more further controls, windows, or other components via the user interface 400 by which the user 106 may increase or decrease a belt speed associated with one or more of the executable controls 420, 422, 424, may increase or decrease a deck incline associated with one or more of the executable controls 426, 428, 430, and/or may modify (e.g., customize) one or more settings associated with any of the other executable controls provided via the user interface 400. It is understood that any such modifications may be saved and/or otherwise associated with the user profile of the user 106, and may be accessed, recalled, and/or otherwise utilized upon accessing the user profile on the exercise machine 102 and/or on other exercise machines 102. For example, any such modified settings may automatically be used (e.g., may automatically be associated with one or more respective executable controls of the user interface 400) when the user 106 participates in a future exercise class via the exercise machine 102. Additionally, in some embodiments the window 418 may be omitted from the user interface 400. In such embodiments, one or more of the executable controls 420, 422, 424, 426, 428, 430, 434 described above with respect to the window 418 may be displayed and/or otherwise provided via the user interface 400 without the window 418.

Figure 5:
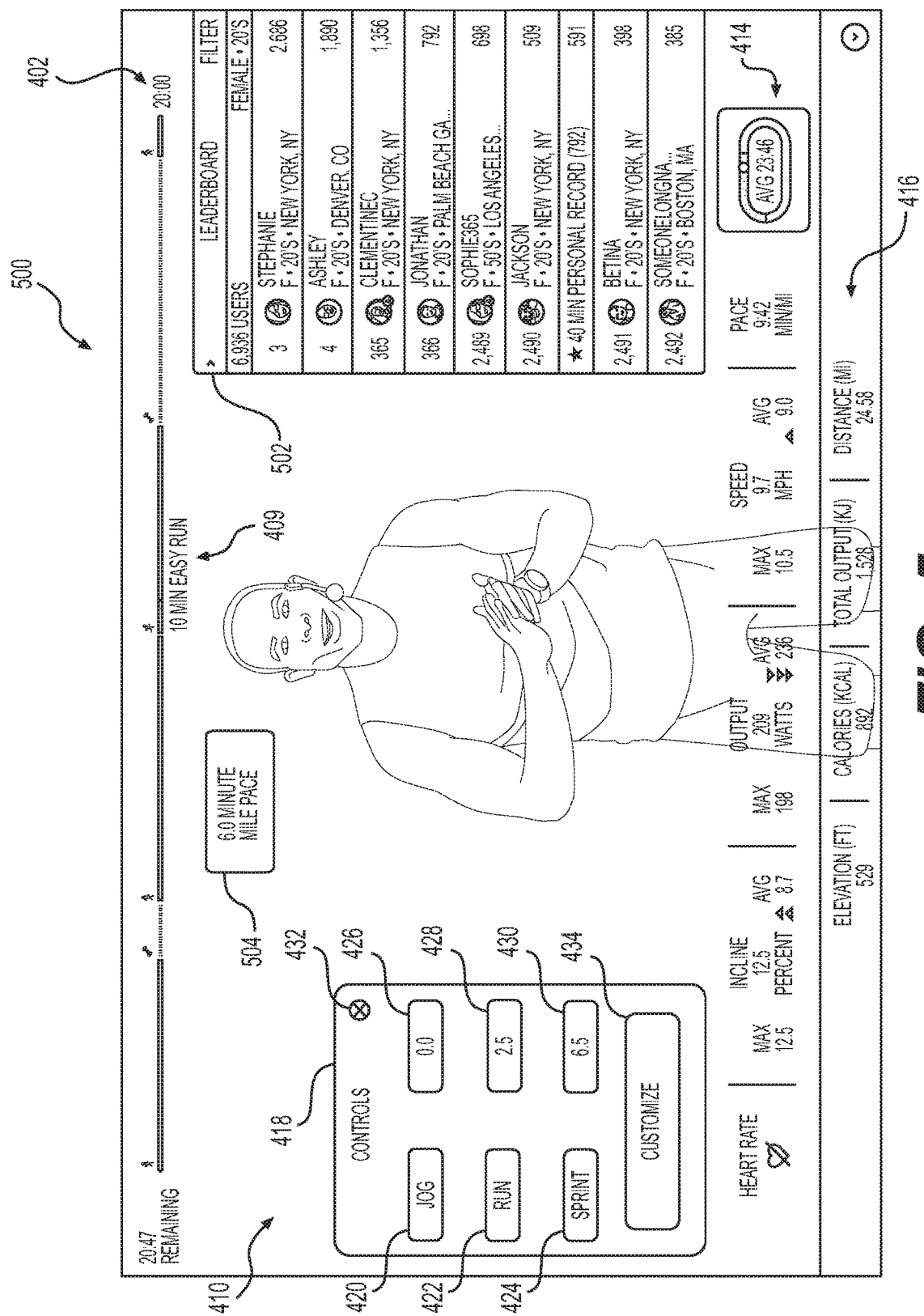
FIG. 5 illustrates another example user interface of the present disclosure showing an exercise class and a leaderboard.

FIG. 5 illustrates another example user interface 500 of the present disclosure. In such examples, the user interface 500 may be substantially similar to the user interface 400 described above with respect to FIG. 4 and/or may be substantially similar to the user interface 200 described above with respect to FIG. 2. As shown in FIG. 5, such an example user interface 500 may include, among other things, a leaderboard 502 that is displayed so as to allow the user 106 to see his or her performance in comparison to other users participating in the same exercise class. In various exemplary embodiments, a leaderboard 502 may comprise a separate window overlaid on and/or otherwise displayed together with the primary window 410. An example leaderboard 502 may be configured to display the relative performance of all participants, and/or of one or more subgroups of participants. For example, the user 106 may be able to select a leaderboard 502 that shows the performance of participants in a particular age group, male participants, female participants, male participants in a particular age group, participants in a particular geographic area, etc. For instance, in the example shown in FIG. 5, the leaderboard 502 has been configured to show the performance of a group of female participants in their 20's. Users 106 may have the ability to individually curate and/or otherwise configure a leaderboard 502, or have the local system 100 curate a leaderboard 502 by selecting an appropriate group of participants relative to the user 106. Users 106 may be able to curate their own leaderboards 502 for specific previously recorded classes to create a leaderboard 502 that provides the maximum personal performance incentive to the user 106.

Users 106 may also be provided with the ability to deselect the leaderboard 502 entirely and remove it from the user interface 500. In various exemplary embodiments, the exercise machine 102 may incorporate various social networking aspects such as allowing the user 106 to follow other participants, or to create groups or circles of participants. User lists and information may be accessed, sorted, filtered, and used in a wide range of different ways. For example, other users can be sorted, grouped and/or classified based on any characteristic including personal information such as age, gender, weight, or based on performance such as current power output, speed, or a custom score.

The leaderboard 502 may be fully interactive, allowing the user 106 to scroll up and down through the participant rankings, and to select a participant to access their detailed performance data, create a connection such as choosing to follow that participant, or establish direct communication such as through an audio and/or video connection. The leaderboard 502 may also display the user's personal best performance in the same or a comparable class, to allow the user 106 to compare their current performance to their previous personal best. In some examples, such performance information may also be displayed in one or more of the display bars 414, 416. The leaderboard 502 may also highlight certain participants, such as those that the user 106 follows, or provide other visual cues to indicate a connection or provide other information about a particular entry on the leaderboard 502.

In various exemplary embodiments, the leaderboard 502 may also allow the user 106 to view their position and performance information at all times while scrolling through the leaderboard 502. For example, if the user 106 scrolls up toward the top of the leaderboard 502 such as by dragging their fingers upward on the display 104, when the user 106 reaches the bottom of the leaderboard 502, it may lock in position and the rest of the leaderboard 502 will scroll underneath it. Similarly, if the user 106 scrolls down toward the bottom of the leaderboard 502, when the user's window reaches the top of the leaderboard 502, it may lock in position and the rest of the leaderboard 502 will continue to scroll underneath it. In various exemplary embodiments, performance information about other users may also be presented on the leaderboard 502 or in any other format, including formats that can be sorted by relevant performance parameters. Users may elect whether or not to make their performance available to all users, select users, and/or instructors, or to maintain it as private so that no one else can view it.

As shown in FIG. 5, the example user interface 500 may also include one or more executable controls 504 that are generated based at least in part on a verbal command from an instructor of an exercise class. For example, the executable control 504 may correspond to the particular exercise class that the user 106 is currently participating in, and the executable control 504 may be provided to the user 106 via the user interface 500 while the user 106 is participating in the exercise class using the exercise machine 102. Additionally, the executable control 504 may be operable to modify one or more parameters of the exercise machine 106 in response to one or more touch inputs. In such examples, the executable control 504 may be embedded within, linked to, and/or otherwise associated with a part of a video file comprising audio and video of the exercise class being presented via the user interface 500. In particular, the executable control 504 may be linked to a part of the video file of the exercise class that corresponds to a timestamp associated with the verbal command uttered by the instructor of the exercise class. In such examples, upon displaying the exercise class via the user interface 500 (e.g., either in substantially real time via live streaming, and/or upon playback of the exercise class using an archived video file), the processor of the digital hardware 148 may provide the executable control 504 via the user interface 500 at the point in time during the exercise class in which the instructor uttered the verbal command.

In example embodiments, the executable control 504 may be substantially similar to an/or the same as one or more of the executable controls 420, 422, 424, 426, 428, 430 described above with respect to FIG. 4. For example, the executable control 504 may correspond to an exercise class currently being performed by an instructor, and the executable control 504 may be operable to modify one or more parameters of the exercise machine 102 that the user 106 is using to participate in the exercise class. For example, the executable control 504 may be configured to modify a speed of the belt 120 of the exercise machine 102 being utilized by the user 106, an incline of the deck 112 relative to the support surface on which the exercise machine 102 is disposed, a resistance of the belt 120, a pedal cadence, a braking force or resistance, and/or any other such parameters of the exercise machine 102.

For example, in some embodiments the instructor may utter a relatively specific command during an exercise class. Examples of such relatively specific commands may include, among other things, "run at a 6-minute mile pace," "go to a 5.0 incline," "reach your Zone 4 power output for the next 2 minutes," or any other relatively definite command corresponding to a desired speed of the belt 120, a desired running speed of the user 106, a desired incline of the deck 112, a desired power zone of the user 106, a desired output level of the user 106, a desired pedal cadence, and/or any other such parameter. Such commands may correspond to the current segment and/or current part of the exercise class. In response, an operator of the server 302, and/or any other operator of a control station associated with the studio in which the instructor is performing the exercise class, may identify the verbal command uttered by the instructor, and may generate the executable control 504 based at least in part on the command.

In such examples, the operator may identify a timestamp associated with the command (e.g., an elapsed time in a video file comprising audio content, video content, and/or other content corresponding to the exercise class) and/or otherwise identifying the time during the exercise class at which the instructor uttered the command. The operator may embed, link, and/or otherwise associate the executable control 504 with a video file comprising the exercise class. In particular, the operator may link, the executable control 504 to a part of the video file corresponding to the timestamp. As a result, when providing the exercise class to the user 106 via the user interface 500 (e.g., either in substantially real time via live streaming, and/or upon playback of the exercise class using an archived video file), the processor of the digital hardware 148 may provide the executable control 504 via the user interface 500 at the point in time during the exercise class in which the instructor uttered the verbal command.

Additionally or alternatively, it is understood that one or more such executable controls 504 may be generated utilizing natural language processing software and/or other at least partially automated techniques. For example, such natural language processing software operating on the server 302 may identify the verbal command uttered by the instructor during the exercise class, and/or after the exercise class has been completed. In such examples, the natural language processing software may provide an indication of the verbal command to the video encoder 320, and/or other components of the server 302 operable to generate the executable command 504. In such examples, the video encoder 320, and/or other components of the server 302 may generate the executable control 504 based at least in part on such information. In some such examples, the natural language processing software may also provide the indication of the verbal command to one or more operators of the server 302, and such operators may confirm, for example, the accuracy of the identified verbal command and/or the placement of a corresponding executable control 504 within the video file being generated at the server 302.

In additional embodiments, the instructor may utter a relatively abstract or vague command during an exercise class. Examples of such relatively abstract or vague commands may include, among other things, "jog for a few minutes," "let's go up this hill," or any other command that may have a different meaning for respective users 106 participating in the current exercise class, but that may still correspond to the current segment and/or current part of the exercise class being performed by the instructor. In response, an operator of the server 302, and/or any other operator of a control station associated with the studio in which the instructor is performing the exercise class, may identify the verbal command uttered by the instructor, and may generate a corresponding executable control 504 based at least in part on the command.

In such examples, the operator may identify a timestamp associated with the command (e.g., an elapsed time in a video file comprising audio content, video content, and/or other content corresponding to the exercise class) and/or otherwise identifying the time during the exercise class at which the instructor uttered the command. The operator may embed, link, and/or otherwise associate the executable control 504 with a video file comprising the exercise class. Additionally, the operator and/or the server 302 may configure the executable control 504 to affect a corresponding parameter of the exercise machine 102 in a manner that best fits and/or approximates the activity desired by the instructor, and that is tailored to the preferences, previous activities, physical abilities, and/or other characteristics of the particular user 106 participating in the exercise class. For example, the operator and/or the server 302 may configure the executable control 504 such that when a touch input is received via the executable control 504 (e.g., when the executable control 504 is selected by the user 106), the processor of the digital hardware 148 may control and/or modify the speed of the belt 120, the incline of the deck 112, a pedal cadence of a stationary bicycle, a braking force or resistance of the stationary bicycle, and/or one or more other parameters of the exercise machine 102 in a manner that most closely approximates the intent of the instructor and/or the contextual meaning of the command.

For example, based at least in part on identifying the relatively abstract or vague command "jog for a few minutes," the operator may generate an executable control 504 configured to cause the belt 120 to rotate at a 4-minute mile pace, and/or at any other relatively common jogging pace, and such a setting of the executable control 504 may comprise a default setting. Such default settings may be utilized by the operator in situations in which relatively little user data is available corresponding to the particular user 106, a user profile of the user 106 does not include user data associated with a preferred jogging pace, and/or in any other situation in which the operator and/or the server 302 does not have access to adequate information corresponding to the user 106. Alternatively, in examples in which a user profile of the user 106 identifies a preferred jogging pace, and/or in which the database 304 includes stored user data or other information indicating previously selected, previously customized, and/or previously entered jogging speeds of the particular user 106, a weight, height, age, gender, or other physical characteristics of the user 106, and/or other such information, the operator may generate an executable control 504 configured to cause the belt 120 to rotate at a jogging pace that corresponds to such user-specific information.

In particular, in any of the examples described herein in which a relatively vague or abstract command has been identified, the operator of the server 302 may generate an executable control 504 corresponding to such a command, and upon receiving a touch input via the executable control 504 while the exercise class is being presented to the user 106 via the user interface 500, the processor of the digital hardware 148 may determine an appropriate response (e.g., an appropriate modification of one or more parameters of the exercise machine 102) based on user data stored within a memory of the digital hardware 148 and/or stored within the database 304 associated with the server 302. As noted above, such an appropriate response, may comprise a default setting (e.g., a default jogging speed, and/or a default deck incline associated with jogging), a previously selected, previously customized, and/or previously entered setting (e.g., a jogging speed and/or a jogging deck incline included in the user profile of the user 106), and/or a setting that is determined by the processor of the digital hardware 148 and/or by the processor of the server 302 based at least in part on user data (e.g., aggregate user data corresponding to the user 106 participating in one or more previous exercise classes using the exercise machine 102) stored within a memory of the digital hardware 148 and/or stored within the database 304.

Figure 6:
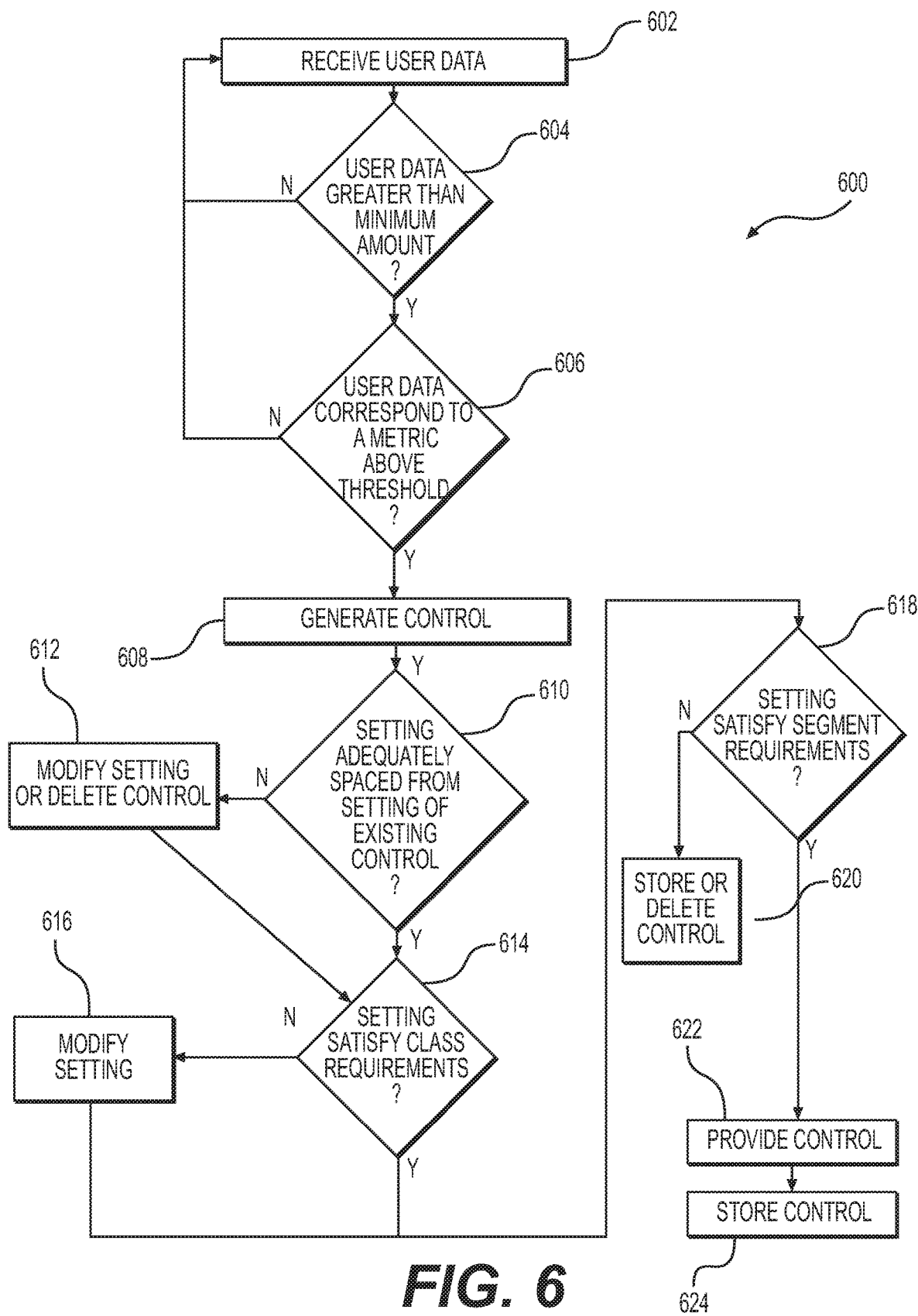
FIG. 6 illustrates a flowchart indicative of an example method of the present disclosure.

FIG. 6 illustrates a flow chart depicting an example method 600 of the present disclosure. The example method 600 is illustrated as a collection of steps in a logical flow diagram, which represents operations that can be implemented in hardware, software, or a combination thereof. In the context of software, the steps represent computer-executable instructions stored in memory. When such instructions are executed by, for example, the processor of the digital hardware 148 and/or by one or more processors of the server 302 described above, such instructions may cause the processor of the digital hardware 148 and/or the one or more processors of the server 302 to perform the recited operations. Such computer-executable instructions may include routines, programs, objects, components, data structures, and the like that perform particular functions or implement particular abstract data types. The order in which the operations are described is not intended to be construed as a limitation, and any number of the described steps can be combined in any order and/or in parallel to implement the process. For discussion purposes, and unless otherwise specified, the method 600 is described with reference to the local system 100, the exercise machine 102, the user 106, the user interfaces 200, 400, and/or other items shown in FIGS. 1-5. In particular, although any part of and/or the entire method 600 may be performed by the one or more processors of the server 302, and/or other components of the networked exercise system 300, unless otherwise specified, the method 600 will be described below with respect to the processor of the digital hardware 148 for ease of description.

With reference to FIG. 6, at 602 the processor of the digital hardware 148 may receive user data associated with a user 106 participating in an exercise class using the exercise machine 102. For example, as described above, the exercise machine 102 may include one or more sensors 147 configured to sense, collect, measure, and/or otherwise determine performance metrics of the user 106, parameters of the exercise machine 102, and/or other information. For example, one or more such sensors 147 may comprise a heart rate monitor, a proximity sensor, and/or other biometric sensor configured to sense, collect, measure, and/or otherwise determine a heart rate, a blood pressure, a body temperature, and/or other physical characteristics of the user 102 as the user participates in an exercise class using the exercise machine 102. The exercise machine 102 may also include one or more additional sensors configured to sense, collect, measure, and/or otherwise determine a speed of the belt 120, an incline of the deck 112, a resistance of the belt 120, a rotational speed of an output shaft of the motor utilized to drive the belt 120, a position of an output shaft of the motor utilized to modify the incline of the deck 112 relative to the support surface on which the exercise machine 102 is disposed, a pedal cadence of a stationary bicycle, a braking force or resistance of the stationary bicycle, and/or other parameters of the exercise machine 102. In such examples, the one or more sensors 147 may include, among other things, a proximity sensor, an accelerometer, a gyroscope, and/or other sensors configured to determine speed, motion, position, and/or other parameters. In any of the examples described herein, at 602 one or more such sensors 147 may provide signals (e.g., continuously, substantially continuously, and/or at regular intervals) to the processor of the digital hardware 148 including such user data and/or other information.

Additionally, at 602 the processor of the digital hardware 148 may receive electronic content via the network 306 described above. In such examples, such electronic content may comprise, among other things, one or more signals from the server 302 and/or other components of the networked exercise system 300, and such signals may comprise any of the user data described above. Additionally and/or alternatively, such electronic content may comprise, among other things, an exercise class. For example, the user 106 may utilize the exercise machine 102 to participate in a live exercise class being streamed in substantially real-time, and in such examples, the electronic content may comprise one or more video files (e.g., a live stream) comprising audio content, video content, and/or other content associated with the live exercise class. Alternatively, the user 106 may utilize the exercise machine 102 to participate in an archived (e.g., previously recorded) exercise class, and in such examples, the electronic content may comprise one or more video files comprising audio content, video content, and/or other content associated with the archived exercise class.

Further, in any of the examples described herein, at 602 the processor of the digital hardware 148 may receive a plurality of user data corresponding to various exercise classes. For example, at 602 the processor of the digital hardware 148 may receive first user data corresponding to a first exercise class that the user 106 is currently participating in using the exercise machine 102, or that the user 106 previously participated in using the exercise machine 102. Further, at 602 the processor of the digital hardware 148 may receive additional user data corresponding to one or more additional exercise classes (e.g., a second exercise class, a third exercise class, etc.) that the user 106 previously participated in using the exercise machine 102. In any such examples, the user data received at 602 may be stored locally (e.g., in a memory of the digital hardware 148) and/or remotely (e.g., in the database 304 associated with the networked exercise system 300). Additionally, it is understood that the user data received at 602 may comprise a plurality of belt speeds, a plurality of deck incline settings, a plurality of belt resistances, and/or any other collection of parameters that the user 106 selected, entered, and/or otherwise utilized while the user 106 participated in one or more respective exercise classes (e.g., a plurality of exercise classes) using the exercise machine 102. Such user data may be received at 602 for each exercise class participated in by the user 106.

At 604, the processor of the digital hardware 148 may determine whether the user data received at 602 comprises greater than a minimum amount of user data required to generate an executable control of the present disclosure. For example, in order to determine, with a relatively high degree of confidence, one or more settings of an executable control being generated by the processor of the digital hardware 148, the processor may determine whether a minimum amount of user data has been received. For instance, in embodiments in which user data associated with only a single exercise class (e.g., a minimum amount equal to two exercise classes) has been received at 602, the processor may determine that the amount of user data received at 602 is less than the minimum required amount (604—No). On the other hand, in embodiments in which user data associated with three or more exercise classes (e.g., a minimum amount equal to two exercise classes) has been received at 602, the processor may determine that greater than a minimum required amount of user data (e.g., first user data associated with a first exercise class, combined with second user data associated with a second exercise class, and combined with third user data associated with a third exercise class) has been received at 602 (604—Yes).

At 606, the processor of the digital hardware 148 may determine whether the user data received at 602 is characterized by, is indicative of, and/or otherwise corresponds to one or more metrics above a required threshold. For example, even in embodiments in which greater than a minimum amount of user data has been received at 602 (604—Yes), such user data may or may not be sufficient to determine one or more settings of an executable control and/or otherwise sufficient to generate such an executable control. For instance, one or more minimum percentage thresholds, minimum length of time thresholds, frequency ranges, minimum and/or maximum parameter values, and/or other metrics may be established and/or otherwise utilized in the process of generating an executable control. In any of the examples described herein, at 606 the processor of the digital hardware 148 may compare the user data received at 602 with one or more such thresholds and/or other metrics in order to determine whether the received user data satisfies such thresholds and/or other metrics.

For example, in one embodiment, one or more such thresholds and/or other metrics may comprise a minimum percentage threshold (e.g., 20%, 25%, 30%, etc.) associated with the percentage of the total duration of the exercise class that the user 106 selected, entered, and/or otherwise utilized a particular belt speed, deck incline, belt resistance, and/or other parameter of the exercise machine 102 while the user 106 participated in the respective exercise class. In such an example embodiment, if the user 106 utilized a particular belt speed (e.g., a speed corresponding to a 6.0 minute mile pace) for greater than such a minimum percentage (e.g., 20%) of the total duration of the exercise class corresponding to the user data being considered at 606 (606—Yes), the processor of the digital hardware 148 would proceed to step 608. Alternatively, if the user 106 utilized a particular belt speed or less than or equal such a minimum percentage of the total duration of the exercise class corresponding to the user data being considered at 606 (606—No), the processor of the digital hardware 148 would proceed to step 602.

In another example embodiment, one or more such thresholds and/or other metrics may comprise a minimum length of time (e.g., 5 minutes, 10 minutes, 15 minutes, etc.) within and/or during the total duration of the exercise class that the user 106 selected, entered, and/or otherwise utilized a particular belt speed, deck incline, belt resistance, and/or other parameter of the exercise machine 102 while the user 106 participated in the respective exercise class. In such an example embodiment, if the user 106 utilized a particular belt speed (e.g., a speed corresponding to a 6.0 minute mile pace) for a length of time within the duration of the exercise class (e.g., the exercise class corresponding to the user data being considered at 606) greater than such a minimum length of time (606—Yes), the processor of the digital hardware 148 would proceed to step 608. Alternatively, if the user 106 utilized a particular belt speed for a length of time within the duration of the exercise class less than or equal to such a minimum length of time (606—No), the processor of the digital hardware 148 would proceed to step 602. In further example embodiments, as noted above, one or more such metrics or thresholds may comprise a range of belt speeds, range of deck inclines, range of belt resistances, a range of pedal cadences, a range of brake forces or resistances, and/or other ranges of parameters associated with the exercise machine 102. Additionally or alternatively, maximum and/or minimum belt speeds, deck inclines, resistance ranges, and/or other values corresponding to parameters of the exercise machine 102 could also be utilized by the processor of the digital hardware 148 for purposes of comparison at 606.

At 608, the processor of the digital hardware 148 may generate one or more executable controls for a user interface 400 based at least in part on the user data received at 602. For example, as described with respect to FIG. 4, the user interface 400 may include a window 418 overlaid on and/or otherwise displayed together with the primary window 410, and such a window 418 may include one or more executable controls operable to modify a parameter of the exercise machine 102 while the user 106 is participating in an exercise class. As shown in FIG. 4, such an additional window 418 may include a plurality of executable controls configured to modify a speed of the belt 120, an incline of the deck 112, a resistance associated with the belt 120, a pedal cadence of a stationary bicycle, a braking force or resistance of the stationary bicycle, and/or other parameters of the exercise machine 102. For example, such executable controls may include a "jog" executable control 420, a "run" executable control 422, a "sprint" executable control 424, one or more deck incline executable controls 426, 428, 430, and/or other executable controls configured to modify a speed of the belt 120 and/or an incline of the deck 112. In such examples, the speeds associated with the respective executable controls 420, 422, 424 may be default belt speeds stored in a memory of the digital hardware 148 and/or in the database 304. Similarly, the deck inclines associated with the respective executable controls 426, 428, 430 may be default deck incline heights stored in the memory of the digital hardware 148 and/or in the database 304. Alternatively, in other examples the speeds associated with the respective executable controls 420, 422, 424 may be entered, and/or otherwise selected by the user 106 when establishing a user profile unique to the user 106, before the user 106 begins participating in the current exercise class, while the user 106 is participating in the exercise class, and/or at any other time. Similarly, the deck inclines associated with the respective executable controls 426, 428, 430 may be deck incline heights entered and/or otherwise selected by the user 106 in a similar manner. In still further examples, the speeds associated with the respective executable controls 420, 422, 424 and/or the deck inclines associated with the respective executable controls 426, 428, 430 may comprise respective speeds or deck inclines that are identified, calculated, selected, and/or otherwise determined by, for example, the processor of the digital hardware 148 and/or a processor or other component of the one or more servers 306. In such further examples, the speeds associated with the respective executable controls 420, 422, 424 and/or the deck inclines associated with the respective executable controls 426, 428, 430 may be determined based on, for example, aggregate user data associated with past performances or other workouts of the user 106 (e.g., the user data received at 602) and in accordance with the steps 604, 606 described above. In any of the examples described herein, the one or more executable controls generated at 608 may comprise data files, text files, digital files, metadata, settings, requirements, instructions, and/or any other electronic file executable by the processor of the digital hardware 148 to modify at least one parameter of the exercise machine 102.

In example embodiments of the present disclosure, one or more of the executable controls generated at 608 may comprise one or more settings associated with modifying a parameter of the exercise machine 102. For example, as described above, one or more of the executable controls 420, 422, 424 may be configured to change, set, and/or otherwise modify the speed of the belt 120, and the speeds associated with the respective executable controls 420, 422, 424 may comprise respective settings of the executable controls 420, 422, 424. Likewise, one or more of the executable controls 426, 428, 430 may be configured to change, set, and/or otherwise modify the incline of the deck 112, and the incline heights and/or decline heights associated with the respective executable controls 426, 428, 430 comprise respective settings of the executable controls 426, 428, 430.

Additionally, in some examples the user interface 400 may include more than one executable control configured to modify a particular parameter of the exercise machine 102, and in such examples, one or more such executable controls may exist as a component of the user interface 400 prior to the generation of one or more additional executable controls at 608. Accordingly, at 610, the processor of the digital hardware 148 may determine whether one or more of the executable controls generated at 608 includes a respective setting that is adequately spaced from the one or more respective settings of an existing executable control included in the user interface 400. For example, in some situations, the user interface 400 may include a first executable control (e.g., executable control 420) having a first setting (e.g., a belt speed equal to a 6.0 minute mile pace) corresponding to a speed of the belt 120. In such examples, the processor of the digital hardware 148 may generate a second executable control (e.g., executable control 422) having a second setting (e.g., a belt speed equal to a 5.0 minute mile pace) corresponding to the speed of the belt 120. In such examples, at 610 the processor of the digital hardware 148 may determine whether a difference between the first setting of the first executable control (e.g., executable control 420) and the second setting of the second executable control (e.g., executable control 422) exceeds a threshold. In such examples, such a threshold may have any desired value corresponding to the parameter of the exercise machine 102 associated with the various executable controls being considered at 610, an age, gender, weight, health, physical fitness, and/or other physical condition of the user 106, and/or any other characteristics associated with the exercise class being participated in by the user 106. In such examples, if at 610 the processor of the digital hardware 148 determines that the difference between the first setting and the second setting does not exceed such a threshold (610—No), the processor may proceed to 612 where the processor may modify the setting of the newly created executable control in order to satisfy the difference threshold described above. Alternatively, at 612 the processor may delete the executable control generated at 608. On the other hand, if at 610 the processor of the digital hardware 148 determines that the difference between the first setting and the second setting does exceed such a difference threshold (610—Yes), the processor may proceed to 614.

Further, as noted above, in some examples of the present disclosure one or more controls 434 included in the user interface 400 may be operable to receive one or more touch inputs indicative of a request to customize and/or otherwise modify one or more settings of an executable control provided via the user interface 400. For example, in response to receiving a touch input via the control 434, the processor of the digital hardware 148 may provide one or more number pads, text entry fields, slider bars, control wheels, and/or other controls via the user interface 400 configured to receive further input from the user 106. In such examples, the processor of the digital hardware 148 may receive one or more touch inputs via such additional controls, and such touch inputs may be indicative of a requested modification to the setting of at least one of the executable controls 420, 422, 424, 426, 428, 430 included in the user interface 400. In such examples, the processor of the digital hardware 148 may modify the setting of the at least one of the executable controls 420, 422, 424, 426, 428, 430 included in the user interface 400 based at least in part on the one or more touch inputs received via such additional controls.

With continued reference to FIG. 6, in some examples one or more of the executable controls generated at 608 may be provided to the user 106, via the user interface 400, regardless of the various configurations and/or requirements of the exercise class that the user 106 is currently participating in. Alternatively, in other example embodiments one or more requirements associated with the particular exercise class that the user 106 is participating in may be taken into account by the processor of the digital hardware 148 in determining whether to provide the executable control while the user 106 is participating in the particular exercise class, and/or whether to modify one or more settings of the executable control. For example, an "advanced" exercise class may have higher level of difficulty requirements and/or other class-specific performance requirements than a "beginner" exercise class. For instance, example performance requirements of an "advanced" exercise class may dictate that a user 106 participating in such a class be able to sprint at relatively high speeds, for relatively long periods of time, and/or at relatively steep inclines, while corresponding performance requirements of a "beginner" exercise class may be relatively less demanding. For example, an "advanced" exercise class may specify performance requirements comprising a minimum belt speed corresponding to a 5.0 minute mile pace, and/or a minimum deck incline at a level equal to approximately 8 inches as measured between the front end of the exercise machine 102 and a substantially horizontal support surface on which the exercise machine 102 is disposed. An example "beginner" exercise class, on the other hand, may specify performance requirements comprising a minimum belt speed corresponding to an 8.0 minute mile pace, and/or a minimum deck incline at a level equal to approximately 3 inches as measured between the front end of the exercise machine 102 and a substantially horizontal support surface.

In such examples, at 614 the processor of the digital hardware 148 may determine whether a setting (e.g., a belt speed) of the executable control generated at 608 has a value that is greater than or equal to the performance requirement specified by the current exercise class. In such examples, if at 614 the processor of the digital hardware 148 determines that the setting of the executable control generated at 608 has a value that is less than the performance requirement specified by the exercise class (614—No), the processor of the digital hardware 148 may proceed to 616 where the processor may modify the setting of the executable control generated at 608 such that the setting of the executable control satisfies the one or more requirements of the exercise class. At 616, the processor may also verify that any modifications made to the settings do not contradict and/or violate any of the difference (e.g., spacing) thresholds considered at 610. In such examples, the processor of the digital hardware 148 may then proceed to 618. Alternatively, if at 614 the processor of the digital hardware 148 determines that the setting of the executable control generated at 608 has a value that is greater than or equal to the performance requirement specified by the exercise class (614—Yes), the processor of the digital hardware 148 may proceed to 618 without modifying the one or more settings of the executable control generated at 608.

As noted above, an example exercise class of the present disclosure may include one or more exercise segments. Such exercise segments may be characterized by a desired physical activity (e.g., jog, sprint, lift weights, etc.) that the instructor of the exercise class commands the user 106 to perform during the respective exercise segment. In some examples, the user interface 400 may include one or more timelines, such as a segmented timeline 402. An example segmented timeline 402 may include one or more segments 404 corresponding to respective portions, parts, or other exercise segments of the exercise class that the user 106 is currently participating in. The segmented timeline 402 may also include one or more visual indica 408 indicating an activity requirement (e.g., stretch, walk, run, sprint, lift weights, etc.), an equipment requirement (e.g., dumbbells, yoga mat, etc.), and/or other requirement associated with a respective exercise segment of the exercise class. In example embodiments, one or more activity requirements and/or other requirements associated with the respective exercise segments of the exercise class may be taken into account by the processor of the digital hardware 148 in determining whether to provide the executable control generated at 608 while the user 106 is participating in the particular exercise class, and/or whether to store or delete the executable control. For example, such activity requirements of the individual exercise segments may characterize the respective segments as being of a particular type (e.g., a stretching segment, a walking segment, a running segment, a sprint segment, a weight lifting segment, etc.). In such examples, the processor of the digital hardware 148 may only provide the executable control 148 generated at 608 in exercise segments with which the particular executable control corresponds or pertains. For example, an executable control generated at 608 configured to cause the belt 120 of the exercise machine 102 to move or rotate at a speed corresponding to a 5.5 minute mile pace may not correspond or pertain to a stretching segment, a walking segment, or a weight lifting segment. As a result, the processor of the digital hardware 148 may not provide such an executable control during such exercise segments based at least in part on the respective activity requirements associated with such exercise segments.

For example, at 618 the processor of the digital hardware 148 may identify an exercise segment of the exercise class that the user 106 is participating in, and may also identify an activity requirement associated with the exercise segment. At 618, the processor of the digital hardware 148 may also determine whether a setting (e.g., a speed of the belt 120, an incline of the deck 112, a pedal cadence of a stationary bicycle, a braking force or resistance of the stationary bicycle, etc.) of the executable control generated at 608 corresponds to, pertains to, and/or otherwise satisfies the activity requirement associated with the exercise segment. As described above, in such examples the processor of the digital hardware 148 may determine, at 618, whether the setting of the executable control is relevant to the type of exercise segment that the user 106 is currently participating in. In such examples, the exercise segment may be characterized by and/or may include metadata, a classification tag, and/or other information identifying the exercise segment as being of a particular type (e.g., a stretching segment, a walking segment, a running segment, a sprint segment, a weight lifting segment, etc.). The executable control generated at 608 may also be characterized by and/or may include metadata, a classification tag, and/or other information identifying the executable control as being of a particular type (e.g., a walking control, a running control, a sprint control, etc.), and such information may comprise one of the settings of the executable control. Accordingly, in some examples, at 618 the processor of the digital hardware 148 may determine whether the setting of the executable control (e.g., the information identifying the executable control as being of a particular type) corresponds to, pertains to, matches, and/or otherwise satisfies the activity requirement (e.g., information identifying the exercise segment as being of a particular type) of the exercise segment that the user 106 is currently participating in. If not (618—No), the processor of the digital hardware may proceed to 620, and at 620 the processor may store the control in the memory associated with the processor and/or in the database 304. Alternatively, if at 618 the processor of the digital hardware 148 determines that the setting of the executable control corresponds to, pertains to, matches, and/or otherwise satisfies the activity requirement of the exercise segment (618—Yes), the processor may proceed to 622.

At 622, the processor of the digital hardware 148 may provide the executable control, via the display 104, while the user 106 is participating in the particular exercise class. In such examples, and as described above, the executable control provided at 622 may be operable to modify one or more parameters of the exercise machine 102 while the user 106 is participating in the exercise class.

At 624, the processor of the digital hardware 148 may store the executable control in the memory associated with the processor of the digital hardware 148 and/or in the database 304. In some examples, at 624 the processor may associate the executable control, in the memory of the digital hardware and/or in the database 304, with a user profile unique to the user 106. For example, as described above, the user 106 may generate a user profile during a set-up procedure of the exercise machine 102, and may continue to update the user profile, over time, with preferences particular to the user 106, desired exercise machine settings, and/or other information. In such examples, the user profile may be configured such that, when the user profile is accessed on the exercise machine 102, and/or on one or more additional exercise machines 102, the executable control stored in association with the user profile may be provided via a display 104 of such one or more additional exercise machines 102, as the user 106 participates in one or more additional exercise classes.

Figure 7:
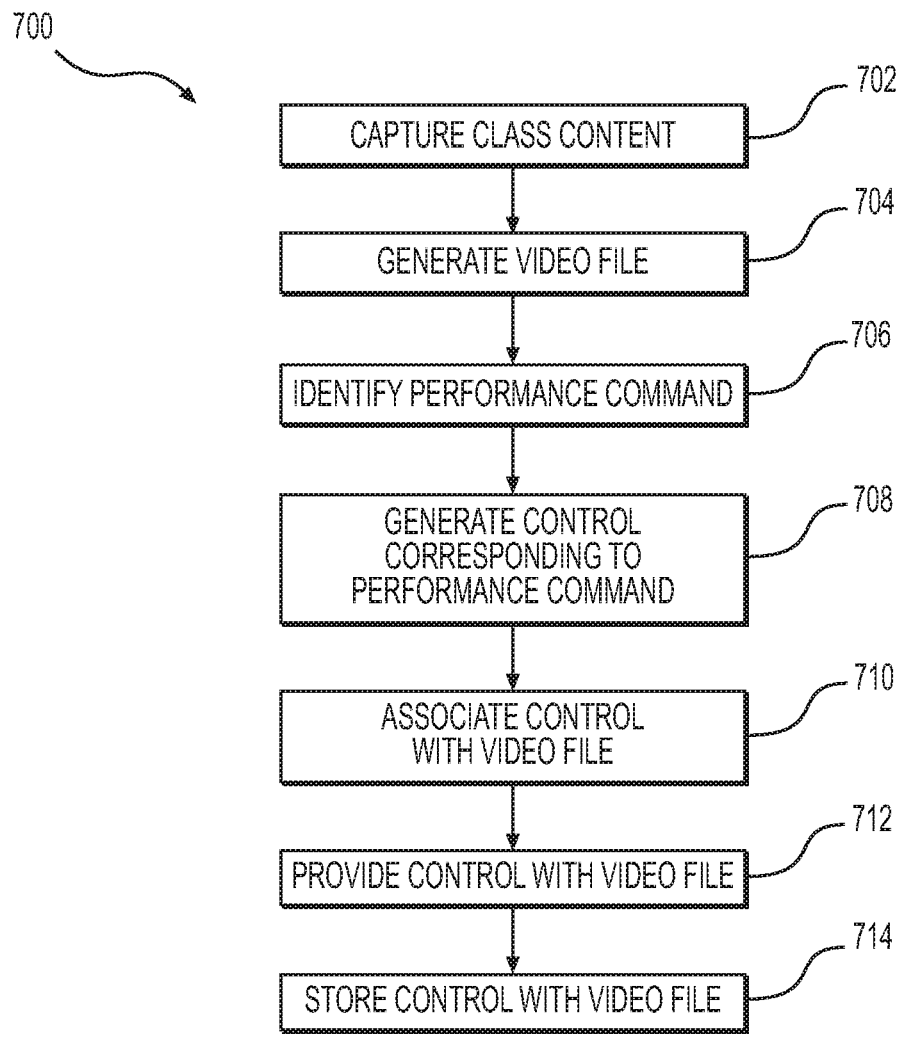
FIG. 7 illustrates a flowchart indicative of another example method of the present disclosure.

FIG. 7 illustrates a flow chart depicting another example method 700 of the present disclosure. Similar to the method 600 described above, the example method 700 is illustrated as a collection of steps in a logical flow diagram, which represents operations that can be implemented in hardware, software, or a combination thereof. In the context of software, the steps represent computer-executable instructions stored in memory. When such instructions are executed by, for example, the processor of the digital hardware 148 and/or by one or more processors of the server 302 described above, such instructions may cause the processor of the digital hardware 148 and/or the one or more processors of the server 302 to perform the recited operations. The order in which the operations are described is not intended to be construed as a limitation, and any number of the described steps can be combined in any order and/or in parallel to implement the process. Additionally, the method 700 may include any of the operations described above with respect to the method 600, and vice versa. For discussion purposes, and unless otherwise specified, the method 700 is described with reference to the networked exercise system 300, an instructor using a first exercise machine 102 to perform an exercise class in a studio or other location comprising one or more of the video cameras 308, microphones 310, and/or other components of the networked exercise system 300, a user 106 using a second exercise machine 102, one or more user interfaces 200, 400, 500, and/or other items shown in FIGS. 1-5. In particular, although any part of and/or the entire method 700 may be performed by the processor of the digital hardware 148, unless otherwise specified, the method 700 will be described below with respect to the one or more processors of the server 302, and/or other components of the networked exercise system 300 for ease of description.

With reference to FIG. 7, at 702 the server 302 and/or other components of the networked exercise system 300 may capture content associated with an exercise class being performed by an instructor. In such examples, the instructor may be utilizing a first exercise machine 102 to perform the exercise class and a studio, gym, and/or other workout facility. In such examples, one or more video cameras 308, microphones 310, music players 312, audio mixers 314, and/or other components of the networked exercise system 300 may be utilized by and/or in conjunction with the server 302 to sense, record, and/or otherwise capture the exercise class content at 702. For example, at 702 the server 302 may capture audio content corresponding to the exercise class being performed by the instructor, as well as video content corresponding to the exercise class.

At 704, the server 302 may generate a video file comprising the audio content, the video content, and/or any other content captured at 702. For example, audio content may be captured at 702 in an audio track, and video content may be captured at 702 in a video track separate from the audio track. In such examples, at 704 the analog to digital converter 316, the video encoder 320, the video transcoder 324, and/or other components of the server 302 may merge the audio track and the video track to form a single digital video file at 704. Additionally or alternatively, the audio content and the video content may be captured at 702 utilizing at least one analog device. In such examples, at 704, the analog to digital converter 316 and/or other components of the server 302 may convert any such analog content to digital content, and may generate a digital video file at 704 comprising digital audio content and digital video content. In still further examples, at 702, the audio content and the video content may be captured in digital form and in a single content capture (e.g., digital recording) process. In such examples, a video file (e.g., a digital video file) may be generated at 702 upon and/or as part of capturing the audio content and video content.

At 706, the server 302 may identify one or more performance commands uttered by the instructor during the exercise class. For example, natural language processing software and/or other voice recognition software operating on the server 302 may identify a verbal command uttered by the instructor during the exercise class, and/or after the exercise class has been completed. In such examples, at 706 the natural language processing software and/or other voice recognition software may provide an indication of the verbal command to the video encoder 320, and/or other components of the server 302 operable to generate an executable command. In some examples, the natural language processing software and/or other voice recognition software may additionally or alternatively provide the indication of the verbal command to one or more operators of the server 302 (e.g., via a display or other output device operably connected to the server 302), and such operators may confirm, for example, the accuracy of the identified verbal command and/or the placement of a corresponding executable control within the video file generated at 704. In still further examples, at 706 the performance command may be identified and/or recognized by an operator viewing the exercise class (in real time and/or upon playback of the exercise class) without the use of natural language processing software and/or other voice recognition software.

As noted above, in some embodiments the instructor may utter a relatively specific command during an exercise class. Examples of such relatively specific commands may include, "run at a 6-minute mile pace," "go to a 5.0 incline," "reach your Zone 4 power output for the next 2 minutes," or any other relatively definite command corresponding to a desired speed of the belt 120, a desired running speed of the user 106, a desired incline of the deck 112, a desired power zone of the user 106, a desired output level of the user 106, a desired braking force or resistance of the exercise machine 102, a pedal cadence of the user 106, and/or any other such parameter. In such examples, at 706 the server 302, an operator of the server 302, and/or any other operator of a control station associated with the location (e.g., a studio) in which the instructor is performing the exercise class, may identify the verbal command uttered by the instructor. In some examples, at 706 natural language processing software and/or other voice recognition software operating on the server 302 may provide an indication of the verbal command to the video encoder 320, and/or other components of the server 302 operable to generate an executable command. Additionally, at 706 the server 302 may identify a timestamp associated with the command (e.g., an elapsed time in the video file generated at 704). Such a timestamp may identify the time during the exercise class at which the instructor uttered the command.

In additional embodiments, the instructor may utter a relatively abstract or vague command during an exercise class. Examples of such relatively abstract or vague commands may include, "jog for a few minutes," "let's go up this hill," or any other command that may have a different meaning for respective users 106 participating in the exercise class, but that may still correspond to the current exercise segment and/or current part of the exercise class being performed by the instructor. In such examples, at 706 the server 302, an operator of the server 302, and/or an operator of a control station associated with the location (e.g., an exercise studio) in which the instructor is performing the exercise class, may identify the relatively abstract verbal command uttered by the instructor. In some examples, at 706 natural language processing software and/or other voice recognition software operating on the server 302 may provide an indication of the verbal command to the video encoder 320, and/or other components of the server 302 operable to generate an executable command. Additionally, at 706 the server 302 may identify a timestamp associated with the relatively abstract command.

At 708, the server 302 may generate an executable control 504 corresponding to the exercise class being performed by the instructor and operable to modify a parameter of an exercise machine 102 (e.g., a second exercise machine 102 used by a user 106 to participate in the exercise class). In particular, at 708 the server 302 may generate an executable control 504 corresponding to the performance command identified at 706. As described above, one or more executable controls 504 generated at 708 may comprise data files, text files, digital files, metadata, instructions, and/or any other electronic file executable by the processor of the digital hardware 148 to modify at least one parameter of the second exercise machine 102. In example embodiments of the present disclosure, one or more of the executable controls 504 generated at 708 may comprise one or more settings associated with modifying a parameter of the second exercise machine 102.

For example, in embodiments in which the command identified at 706 comprises a relatively specific command, the server 302 may configure the executable control 504 such that, when the executable control 504 is processed and/or executed by the processor of the digital hardware 148 (e.g., of the second exercise machine 102), the processor of the digital hardware 148 may cause a component of the exercise machine 102 (e.g., a motor of the deck 112 controlling the speed of the belt 120) to operate and/or perform an action specifically defined by the executable control 504. For example, in embodiments in which an example relatively specific command identified at 706 comprises "run at a 6-minute mile pace," at 708 the server 302 may generate a corresponding executable control 504 that includes instructions, metadata, and/or other information or components which, when executed by the processor of the digital hardware 148, will cause the motor of the deck 112 controlling the speed of the belt 120 to drive the belt 120 to rotate at a belt speed corresponding to a 6-minute mile pace. Similar instructions may be included in an executable control 504 directed to a particular power zone, a particular incline of the deck 112, a particular pedal cadence, a particular stationary bicycle braking resistance, and/or any other parameter of the exercise machine 102.

On the other hand, in embodiments in which the command identified at 706 comprises a relatively vague or abstract command, the server 302 may configure the executable control 504 such that, when the executable control 504 is processed and/or executed by the processor of the digital hardware 148 (e.g., of the second exercise machine 102), the processor of the digital hardware 148 may determine an appropriate (e.g., a best fit) response corresponding to the executable control 504 before causing one or more components of the exercise machine 102 to operate in a modified manner. For example, in embodiments in which an example relatively abstract command identified at 706 comprises "jog for a few minutes," at 708 the server 302 may generate an executable control 504 including instructions, metadata, and/or other information which when executed by a processor of an exercise machine 102 (e.g., a second exercise machine 102) may cause the belt 120 of such an exercise machine 102 to rotate at a 4-minute mile pace, and/or at any other relatively common jogging pace, and such a setting of the executable control 504 may comprise a default setting. Such a default setting may be associated with the executable control 504 at 708 in situations in which relatively little user data is available corresponding to the particular user 106, a user profile of the user 106 does not include user data associated with a setting or preference of the user 106 related to the abstract command identified at 706, and/or in any other situation in which the server 302 does not have access to adequate information corresponding to the user 106. Alternatively, in examples in which a user profile of the user 106 identifies a preferred jogging pace, and/or in which the database 304 includes stored user data or other information indicating previously selected, previously customized, and/or previously entered jogging speeds of the particular user 106, a weight, height, age, gender, or other physical characteristics of the user 106, and/or other such information, at 708 the server 302 may generate an executable control 504 configured to cause the belt 120 to rotate at a jogging pace that corresponds to such user-specific information.

In any of the examples described herein in which a relatively vague or abstract command has been identified, the server 302 may generate an executable control 504 at 708 corresponding to such a command, and upon receiving a touch input via the executable control 504 while the exercise class is being presented to the user 106 via the user interface 500, the processor of the digital hardware 148 may determine an appropriate response (e.g., an appropriate modification of one or more parameters of the exercise machine 102) based on user data stored within a memory of the digital hardware 148 and/or stored within the database 304 associated with the server 302. As noted above, such an appropriate response, may comprise a default setting (e.g., a default jogging speed, and/or a default deck incline associated with jogging), a previously selected, previously customized, and/or previously entered setting (e.g., a jogging speed and/or a jogging deck incline included in the user profile of the user 106), and/or a setting that is determined by the processor of the digital hardware 148 and/or by the processor of the server 302 based at least in part on user data (e.g., aggregate user data corresponding to the user 106 participating in one or more previous exercise classes using the exercise machine 102) stored within a memory of the digital hardware 148 and/or stored within the database 304.

At 710 the server 302 may embed, link, and/or otherwise associate the executable control 504 with the video file generated at 704 such that playback of at least part of the video file by the processor of the digital hardware 148 (e.g., by the processor of the second exercise machine 102) via the display 104 may result in display of the executable control 504. In particular, at 710 the server 302 may link the executable control 504 to a part of the video file corresponding to the timestamp associated with the command and identified at 706. In such examples, the timestamp may comprise an elapsed time of the video file generated at 704 and/or during the exercise class at which the instructor uttered the command. As a result, when providing the exercise class to the user 106 via the user interface 500 (e.g., either in substantially real time via live streaming, and/or upon playback of the exercise class using an archived video file), the processor of the digital hardware 148 (e.g., the processor of the second exercise machine 102) may provide the executable control 504 at the point in time during the exercise class in which the instructor uttered the verbal command.

At 712, the server 302 may provide the executable control 504, together with the video file generated at 704, to the processor of the digital hardware 148. In such examples, the video packetizer 326 of the server 302 may provide one or more signals to the exercise machine 102 (e.g., the second exercise machine 102) via the network 306, and such signals may include, at least part of the video file and/or the executable control 504 embedded therein. In some examples, such as an example in which a user 106 is live streaming the exercise class in substantially real-time, the server 302 may provide the video file generated at 704 and the executable control 504 generated at 708, via the network 306, as part of a live stream of the exercise class. Alternatively, in examples in which the user 106 is participating in an archived exercise class, at 712, the server 302 may provide the video file generated at 704 and the executable control 504 generated at 708, via the network 306, as part of a transmission of the archived exercise class. It is understood that, upon receipt of the executable control 504, a processor of the digital hardware 148 (e.g., a processor of the second exercise machine 102) may cause one or more components of the exercise machine 102 to modify a parameter of the exercise machine 102 based at least in part on the processor executing the executable control 504.

Further, at 714, the server 302 may save and/or otherwise store the executable control 504 generated at 708 together with the video file generated at 704. In such examples, the executable control 504 may be linked to, embedded within, associated with, and/or otherwise stored with the video file such that, upon playback of the video file, the executable control 504 may be displayed as part of a user interface 500 presented to the user 106 via the display 104. Further, while the previous disclosure indicates that the server 302 may perform one or more operations of the method 700, in any of the examples described herein, any of the operations described above with respect to the method 700 may be performed, in whole or in part, by the server 302, an operator of the server 302, an operator of a control station at which an exercise class is being performed by an instructor, and/or by any combination thereof.

Figure 8:
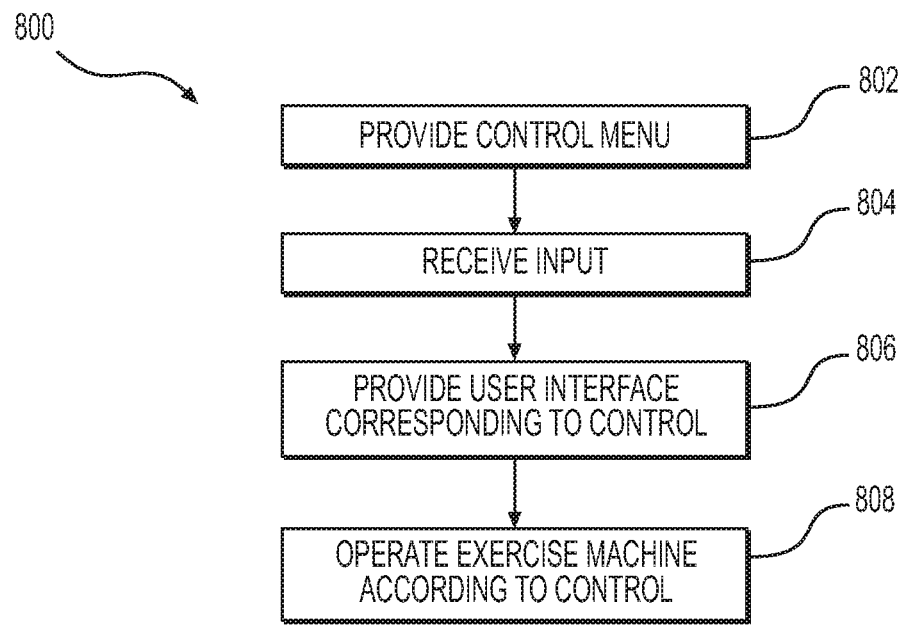
FIG. 8 illustrates a flowchart indicative of still another example method of the present disclosure.

FIG. 8 illustrates a flow chart depicting still another example method 800 of the present disclosure. Similar to the methods 600, 700 described above, the example method 800 is illustrated as a collection of steps in a logical flow diagram, which represents operations that can be implemented in hardware, software, or a combination thereof. In the context of software, the steps represent computer-executable instructions stored in memory. When such instructions are executed by, for example, the processor of the digital hardware 148 and/or by one or more processors of the server 302 described above, such instructions may cause the processor of the digital hardware 148 and/or the one or more processors of the server 302 to perform the recited operations. The order in which the operations are described is not intended to be construed as a limitation, and any number of the described steps can be combined in any order and/or in parallel to implement the process. Additionally, the method 800 may include any of the operations described above with respect to the methods 600, 700, and vice versa. For discussion purposes, and unless otherwise specified, the method 800 will be described with respect to the local system 100, exercise machine 102, user 106, one or more user interfaces 200, 400, 500, and/or other items shown in FIGS. 1-5. In particular, although any part of and/or the entire method 800 may be performed by the one or more processors of the server 302 and/or other components of the networked exercise system 300, unless otherwise specified, the method 800 will be described below with respect to the processor of the digital hardware 148 (e.g., the processor of the exercise machine 102 shown in FIG. 1) for ease of description.

In any of the example embodiments described herein, the local system 100 and/or the networked computing system 300 may be operable to assist a user 106 in achieving one or more workout targets or goals. Such targets or goals may be, for example, a best time for a 5 mile run performed by a particular user 106, a longest distance ran by the user 106 in a particular length of time (e.g., a longest distance ran by the user 106 in 30 minutes), a highest output or calorie burn by the user 106 in a particular length of time, a best time for a 5 mile run performed by another user 106 (e.g., a friend, favorite user, workout partner, spouse, or colleague of the user 106), etc. In some examples, information associated with such targets or goals may be stored within a memory of the digital hardware 148 and/or in the database 304. In such examples, such information may be accessed and utilized by a processor of the digital hardware 148 and/or by the server 302 in order to generate and provide one or more executable controls corresponding to a target or goal of the user 106.

For example, with reference to FIG. 8, at 802 the processor of the digital hardware 148 may provide a control menu, via the display 104 of the exercise machine 102. In some examples, such a control menu may comprise, among other things, one or more windows, sections, and/or other portions of a user interface 400 displayed by the display 104. For example, in some embodiments, such a control menu may comprise one or more windows 418 displayed within the primary window 410. Such an example window 418 may be substantially similar to and/or the same as the window 418 described above with respect to FIG. 4. In such examples, the window 418 may include, among other things, one or more executable controls corresponding to one or more targets or goals of the user 106. For example, one or more such executable controls provided via the window 418 may be operable to modify a parameter of the exercise machine 102, while the user 106 is utilizing the exercise machine 102. In such examples, the window 418 may comprise one or more lookup menus, and each of the executable controls provided via the window 418 may correspond to, for example, a 5 mile run previously performed by the user 106, a longest distance ran by the user 106 in a particular length of time, a workout corresponding to a highest output or calorie burn by the user 106, a best time for a 5 mile run performed by a friend, favorite user, workout partner, spouse, or colleague of the user 106, a multi-session training and/or exercise program that the user 106 may be participating in with one or more additional users 106, and/or any other targets or goals that the user 106 may desire to achieve. In such examples, any of the targets or goals described herein, and/or information associated with machine parameters corresponding to such targets or goals may be stored within the memory of the digital hardware 148 and/or within the database 304 of the networked exercise system 300. Additionally, executable controls corresponding to such targets or goals may also be stored within the memory of the digital hardware 148 and/or within the database 304. It is understood that the method 800 may include any of the processes, and/or other operations described above with respect to generating and/or providing such executable controls.

At 804, the processor of the digital hardware 148 may receive an input corresponding to at least one of the executable controls provided via the user interface 400. For example, at 804, the user 106 may provide a touch input via the display 104 indicating selection of one of the executable controls provided therein. In response, the user interface 400 and/or one or more components of the display 104 may provide a signal to the processor of the digital hardware 148 indicating the selection of the particular executable control.

At 806, the processor of the digital hardware 148 may provide one or more user interfaces corresponding to the executable control that was selected at 804. For example, at 804 the user 106 may select an executable control displayed in the window 418 corresponding to a 5 mile run previously performed by the user 106 (e.g., a best time for a 5 mile run previously performed by the user 106 on a particular course). In such examples, at 806, the processor of the digital hardware 148 may provide a user interface 400 corresponding to the particular target or goal associated with the selected executable control. In the example described above, at 806, the processor of the digital hardware 148 may provide a user interface 400 corresponding to the best time for a 5 mile run previously performed by the user 106. Such a user interface 400 may include, for example, one or more visual images replicating a road, scenery, and/or other items associated with a course of the targeted 5 mile run. Such a user interface 400 may also include a ghosted image of the user 106 performing the targeted 5 mile run along the course. Such a user interface 400 may further include information indicating stored user data (heart rate, blood pressure, output, calories burned, etc.) associated with the targeted 5 mile run, and/or information indicating current user data of the user 106 as the user 106 is participating in the targeted workout.

At 808, the processor of the digital hardware 148 may operate the exercise machine 102, according to the executable control selected at 804. For example, in embodiments in which, at 804, the user 106 selects an executable control displayed in the window 418 corresponding to a 5 mile run previously performed by the user 106, based at least in part on such an input, the processor of the digital hardware 148 may control and/or modify one or more parameters of the exercise machine 102 in order to keep the user 106 on pace for the targeted 5 mile run. For example, the processor of the digital hardware 148 may adjust the incline of the deck 112, the speed of the belt 120, a resistance of the belt 120, and/or any other parameters of the exercise machine 102 according to corresponding settings, and/or parameters associated with the targeted 5 mile run. In this way, the exercise machine 102 may operate, in real time, according to all portions of the targeted run to ensure that the user 106 stays on and/or ahead of the targeted pace, and that the user 106 experiences the conditions and parameters of the exercise machine 102 corresponding to the targeted run.

CONCLUSION

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the spirit and scope of the present invention, which is set forth in the following claims.

What is claimed is:

1. A method, comprising:
receiving, with a processor associated with an exercise machine, electronic content via a network, the electronic content comprising an exercise class;
receiving, with the processor, user data associated with a user participating in the exercise class using the exercise machine;
generating, with the processor and based at least in part on the user data, an executable control unique to the user; and
providing the executable control unique to the user, via a display of the exercise machine, while the user is participating in the exercise class, wherein the executable control unique to the user is operable to modify a parameter of the exercise machine while the user is participating in the exercise class.

2. The method of claim 1, wherein the exercise machine comprises a first treadmill, the exercise class comprises a running class performed by an instructor at least partially on a second treadmill, and the user data indicates at least one of:
a speed of a belt associated with a deck of the first treadmill, and
an incline of the deck.

3. The method of claim 1, wherein the exercise class comprises a first class of a plurality of exercise classes, and the user data comprises first user data, the method further comprising:
receiving, with the processor, second user data associated with the user participating in a second exercise class of the plurality of exercise classes;
determining that the first user data, combined with the second user data, comprises greater than a minimum amount of user data; and
generating the executable control unique to the user based at least in part on determining that the first user data, combined with the second user data, comprises greater than the minimum amount of user data.

4. The method of claim 3, wherein the first exercise class has a first duration, the method further comprising:
determining that the first user data corresponds to a first length of time within the duration;
determining that the second user data corresponds to a second length of time greater than or equal to the first length of time;
determining that the first length of time exceeds a threshold length of time; and generating the executable control unique to the user based at least in part on determining that the first length of time exceeds the threshold length of time.

5. The method of claim 1, wherein the executable control unique to the user comprises a first executable control unique to the user having a first setting corresponding to the parameter, the method further comprising:
providing a second executable control unique to the user, via the display and while the user is participating in the exercise class, wherein the second executable control unique to the user is operable to modify the parameter of the exercise machine, the second executable control unique to the user having a second setting corresponding to the parameter; and
determining that a difference between the first setting and the second setting exceeds a threshold, wherein the first executable control unique to the user is provided based at least in part on the difference.

6. The method of claim 1, wherein the exercise class is characterized by a level of difficulty requirement, and the executable control unique to the user includes a setting, the method further comprising:
determining that the setting satisfies the level of difficulty requirement, wherein the executable control unique to the user is provided based at least in part on determining that the setting satisfies the level of difficulty requirement.

7. The method of claim 1, wherein the exercise class comprises at least one exercise segment characterized by an activity requirement, and the executable control unique to the user includes a setting, the method further comprising:
determining that the setting satisfies the activity requirement of the at least one segment, wherein providing the executable control unique to the user comprises providing the executable control unique to the user while the user is participating in the at least one exercise segment and based at least in part on determining that the setting satisfies the activity requirement.

8. The method of claim 1, wherein the executable control unique to the user being configured to:
receive a touch input from the user via the display, and
modify the parameter of the exercise machine, while the user is participating in the exercise class, based at least in part on the touch input, wherein the parameter of the exercise machine comprises at least one of:
a speed of a belt associated with a deck of the exercise machine, and
an incline of the deck.

9. The method of claim 1, wherein the executable control unique to the user includes a setting corresponding to the parameter, the method further comprising:
receiving a touch input via the display, the touch input being indicative of a requested modification to the setting of the executable control unique to the user; and
modifying the setting of the executable control unique to the user, based at least in part on the touch input, during the exercise class.

10. The method of claim 1, further comprising associating the executable control unique to the user, in a memory associated with the processor, with a user profile unique to the user, the user profile being configured such that, when the user profile is accessed on an additional exercise machine, the executable control unique to the user may be provided, via a display of the additional exercise machine, as the user participates in an additional exercise class.

11. An exercise machine, comprising:
a processor operably connected to a network;
a display operably connected to the processor and configured to display electronic content received, by the processor, via the network;
a deck configured to move relative to a surface supporting the exercise machine;
a belt rotatable about the deck;
a first motor operably connected to the processor and configured to drive the belt; and
a second motor operably connected to the processor and configured to change a position of the deck relative to the support surface, wherein the processor is configured to:
cause display of the electronic content via the display, the electronic content comprising an exercise class,
receive user data associated with a user participating in the exercise class using the exercise machine,
generate, based at least in part on the user data, an executable control unique to the user, and
provide the executable control unique to the user, via the display, while causing the display of the electronic content, wherein the executable control unique to the user is operable to modify a parameter of the exercise machine.

12. The exercise machine of claim 11, wherein the processor is further configured to:
receive an input, via the display, indicating a selection of the exercise class, the exercise class comprising a running class performed by an instructor at least partially on a treadmill; and
based at least partly on the input, provide a request to an additional processor via the network, the request comprising a request for the exercise class.

13. The exercise machine of claim 11, further comprising a sensor, wherein the sensor is configured to detect at least one of a speed of the belt and a position of the deck relative to the support surface, and wherein the user data comprises the at least one of the speed of the belt and the position of the deck.

14. The exercise machine of claim 11, wherein the executable control unique to the user comprises a first executable control unique to the user having a first setting corresponding to the parameter, and wherein the processor is further configured to:
provide a second executable control unique to the user, via the display and while the user is participating in the exercise class, wherein the second executable control unique to the user is operable to modify the parameter of the exercise machine while the user is participating in the exercise class, the second executable control unique to the user having a second setting corresponding to the parameter;
determine that a difference between the first setting and the second setting is less than a threshold; and
based at least in part on the difference, modify the first setting of the first executable control unique to the user.

15. The exercise machine of claim 11, wherein the exercise class is characterized by a level of difficulty requirement, the executable control unique to the user includes a setting corresponding to the parameter, and the processor is further configured to:
determine that the setting does not satisfy the level of difficulty requirement; and
based at least in part on determining that the setting does not satisfy the level of difficulty requirement, modify the setting of the executable control unique to the user.

16. The exercise machine of claim 11, wherein the exercise class comprises a first exercise class of a plurality of exercise classes, the user data comprises first user data, the executable control unique to the user includes a setting corresponding to the parameter, and processor is further configured to:

receive second user data associated with the user participating in a second exercise class of the plurality of exercise classes using the exercise machine;

generate the executable control unique to the user based at least in part on the first user data and the second user data; and associate the executable control unique to the user, in a memory associated with the processor, with a user profile unique to the user.

17. A method, comprising:

capturing audio content and video content corresponding to an exercise class being performed by an instructor, the exercise class being performed at least partially on a first exercise machine;

generating a video file comprising the audio content and the video content;

generating, based at least in part on received user data, an executable control unique to the user corresponding to the exercise class, the executable control unique to the user being operable to modify a parameter of a second exercise machine;

associating the executable control unique to the user with the video file such that playback of at least part of the video file by a processor of the second exercise machine, via a display of the second exercise machine, results in display of the executable control; and providing the executable control unique to the user, with the video file, to the processor of second exercise machine via a network.

18. The method of claim 17, further comprising:

identifying a verbal command from the instructor included in the audio content, the command corresponding to the parameter of the second exercise machine; and generating the executable control unique to the user based at least in part on the command.

19. The method of claim 18, further comprising identifying a timestamp associated with the command, wherein associating the executable control unique to the user with the video file comprises linking the executable control unique to the user to a part of the video file corresponding to the timestamp.

20. The method of claim 18, further comprising identifying the verbal command via natural language processing, and using an additional processor separate from the processor of the second exercise machine.

* * * * *